United States Patent [19]
Wu et al.

[11] Patent Number: 6,018,040
[45] Date of Patent: Jan. 25, 2000

[54] FISH INSULIN-LIKE GROWTH FACTOR 11 PROMOTER

[76] Inventors: Jen-Lieh Wu; Jyh-Yih Chen, both of Institute of Zoology, Academia Sinica, Taipei, Taiwan

[21] Appl. No.: 09/118,841

[22] Filed: Jul. 20, 1998

[51] Int. Cl.$^7$ .......................... C07H 21/02; C07H 21/04; C12N 15/00
[52] U.S. Cl. ...................... 536/24.1; 536/23.1; 536/24.1; 435/320.1; 800/25
[58] Field of Search .................................. 800/13, 20, 25; 435/320.1; 536/23.1, 24.1

[56] References Cited

PUBLICATIONS

Chen et al. Isolation and Characterization of Tilapia (Oreochromis mossambicus) Insulin–Like Growth Factors Gene and Proximal Promoter Region, *DNA and Cell Biology*: 17, 359–376, 1998.

Chen et al. Fish Insulin–like Growth Factors and Their Industrial Applications, *Bioindustry*: 9, 1998.

Chen et al. Production of Biologically Active Recombinant Tilapia Insulin–Like Growth Factor–II Polypeptides in *Escherichia coli* Cells and Characterization of the Genomic Structure of the Coding Region, *DNA and Cell Biology*, 16, 883–892, 1997.

Gray et al. Tissue–Specific and Developmentally Regulated Transcription of the Insulin–Like Growth Factor 2 Gene, *DNA* 6: 283–295, 1987.

Koval et al. Characterization of a Salmon Insulin–Like Growth Factor I Promoter, *DNA and Cell Biology*: 13, 1057–1062, 1994.

Kulik et al. The Promoter of the Salmon Insulin–like Growth Factor I Gene is Activated by Hepatocyte Nuclear Factor 1, *JBC*: 270, 1068–1073, 1995.

Hall et al. Functional Analysis of the Rat Insulin–Like Growth Factor I Gene and Identification of an IGF–I Gene Promoter, *DNA and Cell Biology*: 11, 301–313, 1992.

Kavsan et al. Structure of the Chum Salmon Insulin–Like Growth Factor I Gene, *DNA and Cell Biology*: 12, 729–737, 1993.

Kim et al. Structure and Function of a Human Insulin–like Growth Factor–I Gene Promoter, *Molecular Endocrinology*: 5, 1964–1972, 1991.

Chen et al., GenBank Accession No. AF033802, May 1998.

Chen et al., DNA and Cell Biology, vol 17(4), p. 359–76, Apr. 1998.

Shamblott and Chen, GenBank Accession No. M95184, Nov. 1992.

Marcus, GenBank Association No. X16754, May 1995.

Planas et al., General and Comparative Endocrinology, vol. 77, p. 386–396, 1990.

*Primary Examiner*—Bruce R. Campbell
*Assistant Examiner*—S. Chen

[57] ABSTRACT

This present invention relates to the findings of the DNA sequences of fish insulin-like growth factor II (IGF-II) promoter regions and recombinant IGF-II promoters. These DNA sequences are capable of being expressed in eukaryotic cells and fish embryos of another fish species. The integration of the IGF-II promoter regions or recombinant IGF-II promoters into fish of another species results in the creation of a transgenic fish. The results of this invention illustrate that a fish IGF-II promoter not only can act as a growth factor to stimulate the growth and development of fish, but also is capable of being expressed in other eukaryotic cells such as in human cells.

19 Claims, 9 Drawing Sheets

| PRIMER NAME | PRIMER SEQUENCE | SEQ ID NO. |
|---|---|---|
| IGF-I PRIMER1 | 5'-CGGAATTCATGGAAACCCAGCAAAGATAC | 14 |
| IGF-I PRIMER2 | 5'-CGGAATTCTCATTTTGTGACTGACAAAGTTG | 15 |
| IGF-I EXON PRIMER1 | 5'-CGAAGCTTAGATCMAAATTCRAKCCYATTC | 16 |
| IGF-I EXON PRIMER2 | 5'-GTCTCGAGTTGTTTTTACAGTGAACCATTCC | 17 |
| IGF-I EXON PRIMER3 | 5'-CGGGATCCGAAATAAAAGCCTCGCTCTCCACAGA | 18 |
| IGF-I EXON PRIMER4 | 5'-CGGGATCCAATAAACCCAACAGGCTATGGCCCCAGT | 19 |
| IGF-I EXON PRIMER5 | 5'-CGGAATTCGGCCCTGAGACCCTGTGCGGG | 20 |
| IGF-I EXON PRIMER6 | 5'-CGGAATTCAGAAATCTTGGGAGTCTTGAC | 21 |
| IGF-I GSP1 | 5'-CGCTCGAGCGCCCCTGTTGCCGTCGGAG | 22 |
| IGF-I GSP2 | 5'-GGTTGGCCTACTGAAATAAAA | 23 |
| IGF-I P2 PRIMER | 5'-GGAAGCTTATTTTTACATTTTCACTC | 24 |
| IGF-I P3 PRIMER | 5'-CGAAGCTTCGGTGCCAAATTACGCAG | 25 |
| IGF-I P4 PRIMER | 5'-CGCTGCAGGACATTTTCAACAGGAAA | 26 |
| IGF-I P5 PRIMER | 5'-CGAAGCTTGCTGGTGGTGGTGGTGGGGCTG | 27 |
| IGF-I P6 PRIMER | 5'-CGCTGCAGGACTTTGTTCCATTGCGC | 28 |
| IGF-I P7 PRIMER | 5'-GCCTGCAGTTCCAACAAGACAAAGC | 29 |
| IGF-II P3 PRIMER | 5'-GGAAGCTTCATGCCTGCATCTAC | 30 |
| IGF-II P4 PRIMER | 5'-GGAAGCTTCTGCATCAACCCCG | 31 |
| IGF-II P5 PRIMER | 5'-GGAAGCTTAGTGATTCCACTG | 7 |
| IGF-II P6 PRIMER | 5'-GGAAGCTTCATTTTTCTTGGAGTC | 8 |
| IGF-II P7 PRIMER | 5'-CGCTGCAGCCTGTGTGTAAACATTGTGA | 9 |
| IGF-II P8 PRIMER | 5'-GGAAGCTTTGCCCATGGAAGTGTTC | 10 |
| IGF-II P9 PRIMER | 5'-CGCTGCAGTTCAAGCACTTTCATAAAAC | 11 |
| IGF-II P11 PRIMER | 5'-GCGTCGACGTCAGATGGCAGTAGTCAAAATG | 12 |
| GTP1 | 5'-TTCACCGGGGTGGTGCCCATCCTGGTC | 32 |
| GTP2 | 5'-TGAAGAAGATGGTGCGCTCCTGGACGTAGC | 33 |

FIG. 1

TILAPIA IGF-I EXON 1 AND PROMOTER REGION

```
-1213 GAGCTCCTGTATCGGAAGCGTGTGTCAGTGCTGCTGCCTGTGACATTTGA
-1163 TGATGATCGCGTTTTGACCCACTTTACCCAAACAACTCTAACTGTTGCGT
-1113 GTCTTAAGTCCCCTTTGGAACCAACCTTGCTCGTGATGCACACACACAAA
-1063 CACGGACGGAGCATGCCTGGATACGTGCCGGTGTCCTGTTTTATGATTGG
-1013 GTCACAGCACTGATCTCATGTTTAGTGACTGGATCAGTGTTGATATCCCA
 -963 TCACTGCTGAGAACAACCCTCTTTAAGCCCTTGCTTTCGTCCCTTCCTGT
 -913 GACACAGTGGGAACTGCGGGGCCCCGACTTCAACACGATGACAGTGGGTG
 -863 GGCCTGCATCAAGAGTCTGTCAGTGCAAAACAATGGCTCCAGGAATTGAA
 -813 ATTAATGTCTCCTCCATCATAAAACCCCATGTGTTTTTCTTTTTTTCCTC
 -763 CTTTTTTTATTTTTCCACTCTAGTTCACAGGNGCATCAGATGTCATTTAC
 -713 AGGCGAACCCACTTCTATTAAGTGAAAATCAGCAAGAAGGGAGAGAAAAC
 -663 CAGAGACATACACCAGGNTTATGCAGTGACAGTGTGCAGAAAAGGCAGCAA
 -613 ACCCTGCACAGTGGCTCTCAGTTTAGAGGGAACAGGGCTTCACATGTGGC
 -563 TTTCTGGCTCAAGTTTGCTCCTTACTGTAATAAAAAATGTCACATTTTTAC
 -513 ATTTTCACTCCAGTTCACATTTATTTAGCTTTTCCTTGTGAGGTTTTCAG
      P2 PRIMER
 -463 GTGAGGAGCACTGCGGCGTCTAAGTGGGAAAGTGTTTTTAATGATTTATT
 -413 TAATCAAACCATTAGTGGAGAGACTTGGTGGTCAGATACACGGTGCCAAA
 -363 TTACGCACAACAGCAAAGAGCCATATCACAACCGCCAGCTCGTCTTTAAC
      P3 PRIMER
 -313 TTCTCCTTTATGAGCGTTTCAGGGCACAAAATAATGCGTTTGTAAGAGTG
 -263 TGAGCCGCCACTGCTGCTGCTGGTGGTGGTGGTGGGGCTGATCTGAACTA
                                  P5 PRIMER
 -213 CTAACCAAGTCTTAGAGAGATCAAAATTCAATCCCGTTCTGAGAAAAAAC
 -163 AGAAATGACGTTATTTTGAATATGTGCCCAAAATCCTTAATGAATAACTTA
           HNF 5-LIKE           HNF 1-LIKE
           5'RACE
 -113 GGACGAGTAGGAGGCAAATGCTGCCCCAGCTGTTTCCTGTTGAAAATGTC
                                  P4 PRIMER
  -63 TGTGTAATGTAGATAAATGTGAGGGATTTTCTCTCTAAATCCGTCTCCTG
           5'RACE
  -13 TTCGCTAAATCTC|ACTTCTCCAAAACGAGCCTGCGCAATGGAACAAAGTC
                                      P6 PRIMER
   38 GGAATATTGAGATGTGACATTGCCCGCATCTCATCCTCTTTCTCCCTGTT
   88 TTTAATGACTTTAAACAAGTTCATTTTCGTCGGGCTTTGTCTTGTTGGAA
        *                                   P7 PRIMER
  138 AACCGTGGGGATGTCTAGCGCTTTTTCCTTTCAGTGGCATTTATGTGATG
  188 TCTTCAAGgtaacttacctgatttcctttgacactatacattatcacctt
  238 gattcttcacttgctcactatttgcacagagcatcctcgcctactttaaa
  288 aagaaacaataaaaggggattcttatcgcttgcttgtatttcacagcttt
  338 tgaacgcatgcattggtgcggatttattcacattttctcctttcatcc
  388 acttatggaacaactctcccgcatgtcctggtaatctatttatttatt
  438 ttattttccagagataattatattttctacattttgctttaattgattct
  488 tttctcttttttgcaattaaaaaaaaaatcattgacatggatcgtgcatga
  538 ctttcagcgcaggtatgaattttggacattttccgtgcgcccggcgctctt
  588 tttccaccagaaagccctaatgcagctgtgcaactttccaaagtaattac
  638 tgctgagtctgcataatttaagttgctaatatctaacctgatgcctctgg
  688 cggggttgaaagaacgagagcgggagagagagagatttccgaaacacttg
  738 cgggcgtcgggaacttgcgggtgtgaagttaatagataacgtcccgggtt
  788 t
```

TILAPIA IGF-I EXON 2

```
  1 gttaaaagaaactctttttccgatgatgctgtgaaaatgttcttgctctc
 51 tcccctgtgcgcagAGTGCGATGTGCTGTATCTCCTGTAGCCACACCCTC
101 TCACTACTGCTGTGCGTCCTCACCCTGACTCCGACGGCAACAGGGGCGGG
151 CCCTGAGACCCTGTGCGGGGCGGAGCTGGTCGACACGCTGCAGTTTGTCT
201 GTGGAGAGCGAGGCTTTTATTTC......
```

TILAPIA IGF-I EXON 3 AND EXON 4

```
  1 AATAAACCAACAGGCTATGGCCCCAGTGCAAGGCGGTCACGTGGCATCGT
 51 GGACGAGTGCTGCTTCCAAAGCTGTGAGCTGCAGCGCCTTGAGATGTACT
101 GTGCACCTGTCAAGACTCCCAAGATTTCTCGCTCTGTGCGTTCACAGCGG
151 CACACAGACATGCCAAGGCACCCAAGGTTAGTAGCAGAGCGAACAAGGG
201 GACAGAGCGTAGGACAGCGCCTCAGCCAGACAAGACAAAAAACAAGAAGg
251 ttgagctaagcatcaaaacagataaactgtaaaaattgttgattggatcg
301 aatttacatttctgttacatgatcagagcatacgtgcataatatcctgat
351 taattaaggtgatatagcttaataagcagaaactcgtccatccaactaaa
401 gttacctaattttttcttccacagAGACCTTCACCTGGACATAGTTCATCC
451 TTCAAGgtatgcatgcaaaatgatctcatgttcattgtccttttgtcatt
501 taagctttaccaaaacacacaatctctcccatgacataagagtttcaaag
551 caggcgatcttttacagaa
```

TILAPIA IGF-I EXON 5

```
  1 tctatatctctgctgtacatctaaaaaaaaaaaaaaaaaaaaacaaatgt
 51 gttttattttgtttgcagGAAGTCCACCAGAAAAACTCAAGTCGAGGAAG
                                 #
101 TTCGGGGGGCAGAAACTACAGAATGTAGGGAAGGAACAAATGGACAAATG
151 CCCAGCAATTGGGAGGAGAGAAGGGAGTGCCCTTACCTGGTNACCCTGTG
201 GAATGGTTCACTGTAAAACAA
```

FIG. 2

TILAPIA IGF-II PROMOTER REGION

```
-5477 TGGTAAGCTTGCGACCGCCCTAGGACTAGTCTCGAGGCTAGCCCATGGGG
-5427 CGCCGGGCCCGGATCTGTGTTTGGTATATTTGATTTAAACAGGGCTACAC
-5377 AGATCCTGCCTACAGACAGGAGGAGAATGATTGGTGACATTGCCTTCA
-5327 GATACAGATAGTGAGATGGGCCTTTTCCTAAATACTGCGCACACAACCAT
-5277 AAGAAATAGACATAAAAGTGAAATGTAATAATTGTGTGCATATGTTTGTC
-5227 CTCAGTGGGCAGTCGATCCCCAGACTGGAATACACAGAGGAGGAGATCGG
-5177 CACATGGTAAGGGGCTCTTTCACGTTACTTTCCAATATTGATAATATATG
-5127 ACATGAAAAGTTAAGTCTGAAGTAGCAGTGAGAATAAAATCATAATTTAC
-5077 AATGAACACAAAATGTTTTTATCTATTAAAATACGTTTCATTGTTATTTT
-5027 GTTTTACTGTGAACACATTGTGCTCAACCCAGCAACCAATGAGTCATTTG
-4977 CATATGAATGGTCTTTTATGGATGCTTTGGTAAATTTAACTTCAGATGGA
-4927 GGGTGTCACTAGAATAAACTCGAGGTGACAGCTCGAGCTTGTCTGAATGA
-4877 AAAACATATCCATAGCCTGAGAACAAAGTGTTGTTTGCAATTCAATAGAT
-4827 GTTTATCATTTTACTTGAACAGTTTAGGACAAAAAAAAAGGACACTAATG
-4777 AATGAATTTAGTCACCAGACCAAGTAGAAAAATTATAGCAAAGTGCTTTT
-4727 TCATAAGATTTATACGATACAAGAAAAACACAGCATAATAAATAGTTAAA
-4677 CATTGCAGGATAAATCCAATTTAAACACTGTTAATTAGGAGGCGCATAAC
-4627 ACTAACCATAACTCTAAAACTACACTGCAATTTTACTTATTTCCAAAGTT
-4577 TTTCCAAGATTTTGATTTTAATAAATGAAACCTCAATTTTTATGTAATTA
-4527 AATACTGATTTAGGCGAGAAGTATATTCAACCCTGAGGGACTTGTACACC
-4477 ACCCATGCCTGCAGTGAATACCTTGAGGCTTTTCGTCTCCTAGAAAGGCA
-4427 TTGTGGGTACAGCCCAGACAACATTCCCCAGCTGGAAGATGTGTCACGCT
-4377 TCCTCAAAGGTAAAAACGGGATAAGACNAAATGAAAAAAGAAAAGATACC
-4327 TAAATACAGACGCTTAGCAAATGTAGACTCCACCTATCAGGGTTTGGATT
-4277 CTCTCTCTCTCTCTCTCTCTCTCTCTTGCTTACTGTCGCTTCACCA
-4227 CCATCCCCCTGAACACACACGCCAGACGCCACAGGATTTCAGCTGCGTC
-4177 CAGTGGCGGGGCCTGCTCTCAGCCAGAGATTTTCTGGCCAGTTTGGCATT
-4127 CCGAGTGTTCCAGTGCACCCAGTACATCCGACATGCTTCCTCCCCCATGC
-4077 ACTCCCCAGAACCGTGAGTACTACTGTGACTCTTTTGGCTTTGTGCTTCA
-4027 ACTAATTATAAAGTATACAATCAGAAATAGCTCCATAAAAACAAAAGCAA
-3977 GTGAAATTACACATAGCATCTGCTAATAGCAACAACAATTCATATTAAA
-3927 AGCTGCTGTATGCAAAAGCTGTTGTGTTTATGTAATTATTTTAAGATTCA
-3877 ATATGTTTTTCTTTAGAGAACAGGCTTGCTTTCATTCTGTTACTGTTATG
-3827 TAATCAGATTGAATTTCCAGTTTGTGATCATAAAGTCTGCATCCAATCAA
-3777 ACTGAACTGTGTGGTGTTTTTCATTTAAGATCAAACATTGTCGTGAATTA
-3727 ATATAACTGTTGCTTTCTCTTCAGTGACTGCGTCCATGAATTACTGGGCC
-3677 ACGTACCCATGCTGGCTGATCGCACTTTTGCCCAGTTTTCACAGGTTAGT
-3627 GCTGAAACGATTAGCAGCCTTACAGATCATTCAGTTCTTTTGTGCTATTT
-3577 AGCAAGAATTGATCTATTATTTTCCACAGAACCTTGGTTTGGCTTCACTG
-3527 GGGGCTTCGGATGAAGATATTGAGAAACTGTCCACAGTAAGACTTTTGTC
-3477 TTCGAACACAAACAACACATGCAAACTGTATAAAAATTACTGCGGTGAAG
-3427 TTTGGGGTTGAACCTCATGTTGCCAGCCCATCCCCCAACAGAGACACAC
-3377 ACACACACAAACACACACACGCTCCCACGCTTCTTAGCCTGGGCTTCAAG
-3327 CACGAACTGAGATACATATCCCATATAGTAAACAATAGAATTAACTATCG
-3277 CTAAAATATCTTTCAAAATACATTACTTTGGACAGCCTTGTCTAAAATCT
-3227 AACATGTAGCTAATGCACTGATTGTCCATACTTCTTCTCAGTCACCTCCT
-3177 TTCTGTTTTTCCATCAGCTGTACTGGTTCACGGTCGAGTATGGCTTATGT
-3127 AAACAAAATGGTGAGGTGAGGGCTTATGGAGCTGGGCTGCTTTCCTCTTA
-3077 TGGTGAACTTGTGGTAGGTTCACACGTTTTTTTTTTTTTTCTTTAATGCAG
-3027 GACACACAGCAGCTGTGAGCTAATTCTCCATTTTTTTAAACTTCCAGCA
-2977 CTCTCTGTCTGATGAACCAGAGACAAGAGAGTTTGATCCAGAGGCTGCAG
```

```
-2927 CAGTGCAGCCCTATCAAGACCAGACGTACCAGCCTGTTTACTTTATTTCT
-2877 GAGAGTTTTTCAGATGCCAAGGAGAAATTCAGGTACTGCTCTTTATCGTA
-2827 CCAGACATACACCTACATAAGAACATACAGAACTGATAAAAAAAATGTGT
-2757 AAAAAACAACAACGAAAAACAAAAAAGAGAGGGGTTATGTGAGGACGAGG
-2727 TCAGAGAACAGCCAGCCAACCCCGGAGGCCACAAACTATTGTAGGTCAGC
-2677 CATAGCAGCCAGAAGACAGCTGTTCCTAATGTAGTCTTCCTTACCAAGGC
-2627 AAAACTCTGGAGTTTTATTTGGCAAACAGATCAAATGCTGCCCTGCCAAA
-2577 CAAGTATCTTAAGTGAGTGTGTTCACAATATTCAGCCTCTAGTAGAATGC
-2527 AGCACATGACATCTCGGACACACTGGATGAGGAAATACCCGCACTGGAAT
-2477 GTTGAAAGAGCACAGAGAACATTGTGAGCATCATACATAGGAGTATATCT
-2427 CTATGTTGTGGAATCCACAGTCTCAATAATTTGCATGCATGTGCAACATG
-2377 GCAAATTTATAACAACAAGGACAATTTGCAGGCATGGTTGCTTTAGTCCAT
-2327 ACTTTCAGTTGGAGCATAAAGACAGCCCCATTTGAGATCTTTAAGTTTCT
-2277 GACTTCTTTACATCTTTACAATTTTGACCAGGGCTTATGTAGCTGGCATC
-2227 AAGCGTCCCTTCTCAGTCAGATTTGATCCATATACCAGCAGTGTTGAAGT
-2177 ATTGGACAACCCAGTGAAGATCCAAGGAGGCCTGGAAGGTGTGAAGGATG
-2127 AGCTTAAAGTGCTGACAGACGCCCTAAGTGTGCTATCGTGATGATGCGCT
-2077 GTCTTTCACCATCCGCCTGTTGTTTGCTTTTCTCTCCGCTGAGTCCACGC
-1977 AATCTGAGTTTTGCTTGTTGTGTGGTTGGCTGGTTGGCCAGCAAGGTTGCAA
-1927 CCATTAAAACCTCAAAACTCAGCGCTGACAAAGTATCCAAAGATCTTAAA
-1877 TGCTTGCATTTGTGAAATGATGGGGTTTTACTGACTGGACCATTCATGCT
-1827 TTTAAAGTTTGTTGTTTGAGAAATGTGTCAAATCTAGAGTCACATCAAAG
-1777 GGAACTCTGATAATGAAGAATAAAAGGAGGTATATAAGAATGGTATAGAA
-1727 TTTGAAACTAAAGAATTTATAATGGTGAATATTTGGAACATTTATTTTATT
-1677 TAGAAAAAAATCTGTAACTGCTCTGTCAAAAGCTTTATTTTCCAAATATG
-1627 AGAATTTAGCTTTTGAGTAATTAAATCCATAGCTTTCATATGCTGTTCTT
-1577 GTCTTGCATTGTGTATTTTATGCTGGTTTCGTCTTGCAGTGTAAATGCAT
-1527 AATAAAAAAAAAGGGGGGGGGAAGAAAACATAGTTCCTATGTAATAAACT
-1477 ATTGACTACAAACTATCGATAATAAAGAACTGCAAATTAACATTTCACT
-1427 ATCGTTTCTGTGATTTATCAAGTTTTTATTCCTACAGTTAAACTAAAAAT
-1377 ATAAATAATAGCATTATATTTGATAGGTTTTGGCTCTTATCGCTGATGGG
-1327 AAAACCTAGAAATACTTTCACATGAATTATTAGTTAACGACACCTGGCTG
-1277 AGTCTTGCTTTACATTTGTCTATCGCAAGAGGGAGCTGTCTAGCTGTTTT
-1227 CGCCTGCCTCGTCATAAAATCACAGCATATTTATTGAATTTTTTTTTGAG
-1177 AGAATAAATCTTAAGGTTCTCTTCCTGTCACCAATCTCTGTTTTGAGTTA
-1127 AAAACAAGCTAAAGCTCACAAACAACCTCAAGATATTTTAATGACACTAA
-1077 ATGCACTATAGAAACGCTATTTAATGTGCTGTATTGAAAATAAATAAATA
-1027 AATAAATTAAAAATCAGCCGTTTTTGAAAGAGAACACGAGTTTGGTGGGA
-977  GCATAAGAGAGAAAAGTTAAGCTGTGAAAGAGAACACGAGTTTGGTGGGA
-927  CACGCTTCCTTCTGTTCAGGTAAGAAGATGCGATCATATCCAGGATTCAA
-877  CATTCCAGGACAAAAGCTGGAAAAGCCGAAAGCTGGAGGACAAACAAACGG
-827  AGGTACCGTAACCAGACCAGCAGGTGTCAGTATGAGTCTGAAGACACGTG
-777  CAGATCTTTAACTTCACCAGACGCACACACCGAAATAAGGGGCCCTCGAG
-727  TTTCATAAAGCATAACGTGAATGTGCGTGTTTATATGTTAAATTCAGATT
-677  TTCAAAGTATGGATCACTCTTTGTATACTCGGACGGAACCTATTCCATAT
-627  CTGCAATGAAGTAGTGCTGCTGGACTGTACGATGCATATTTGTCATAATG
-577  TGCATACTAATGCATTAGTAAAGCTTTTAAAAAAATCTCCACATTTGTCT
-527  CAATGCTGACTCTCCATCATATGACCATCCATAATATCTGTGGCTTGAGA
-477  CATGCCTGCATCTACTTTCCCACTTGGTGTCCCGCTGCATCCGCTTTCCA
      P3 PRIMER
-427  CTGCATCAACCCCGTTTACTATCTCCCCTTCACTGTCAGGCACCTTTGAC
      P4 PRIMER
```

FIG. 3A

```
-377 CCCAGTGCCTGCATCTACACAGTCTGAGGAAAGCCGCAAACCTTGGCCAC      374 ttttgatttgtatgcagcagagaaagttcaagatgcataaacggcgagga
-327 AGTGATTCCACTGAATGTTAATCTTAATTACAGCAGGGCGGAGACATTGA      424 gaagctttgcggcatttgggatagaaaaagaacaagtaattttagtcttc
     PR PRIMER                        Sp1-LIKE
-277 CATTTTTCTTGGAGTCGAAGGAATTACCCCTATTCTTGTTCAGTCTGCGT      474 tcgcgcctggatggtgtcgtggacacggagcaaacagctgattttttacc
     P6 PRIMER
-227 CCTGTGTGTAAACATTGTGATTGTAGGTTACAGTGCCGTAAACGTGGAAAA    524 ggcagataggggggcggcaggtttgagggtcagtgagctcattccggggtg
     P7 PRIMER
-177 TGCCCATGGAAGTGTTCCATATTTTGTGACTCTCACCCTCTTATTCTCCC      574 agcaaagggaaaatatatgctgagtttggtgttttcggctagttaactat
     P8 PRIMER                                            624 cgagcagccggccttgcaacttcaggatggttgtgtaagagtggaaagct
-127 TTCAAGCACTTTCATAAAACGTCTCTGGGCCTTTTTTTTTTCATGGGCGA      674 ggtgatactggcgacttgtgtttttttcctccagaataagcacttcttca
     P9 PRIMER                                            724 ggtgcgacagacatgacagcagctgataatagcgggcggggaaggtgaag
 -77 AGAGGAGGAGCAAGGGGTGGGGTGGGTGTAAGGGGCGTGCTTTAGTATAT    774 agcgggtctgcacattgtgacttgatttgagatgattttcttttctgaa
                         5'RACE                          824 tttctactttgtcgaacatttgagcacgtacaccgtacacaccgggagcc
 -27 AATACCTCTCCCTGAGAAGTTTTGCCTGTCGCCTAGTCTTTGGGACAGCT    874 tgtgatgaagactgtaccctcttcgtctgaaaaaaaaaaaaaaactctg
  24 TCTCACTCACCATCTCTATAGTTTAACCAACTGGGAAACTAACTCACCTG    924 gctgattttgattaaaaaaatggtatttaactgtcattaactgttatttt
  74 CAATCACACCAACCAAATAATTCCCAACATTTTGACTACTGCCATCTGAC    974 gttaacgatttctgtatgccacaacttctgactatcatggctacatttg
     *                               P11 PRIMER         1024 gtgaccccatgcttcataccgcagGTCAAGAAGATGTCTTCCACGAATC
 124 ATGGAAACCCAGCAAAGATACGGACATCACTCACTTTGCCACACCTGCCG   1074 CCGCGCTGCTCTTTGCACTGGCCCTGACGCTCTACCTAATGGAAATGCC
 174 GAGAACGCAGAACAGCAGATGAAGgtaaccaaagaacaagcaaattgtt    1124 TCCGCGGAAACCCTGTTTGGGGGAAAACTGGTGGATGCGCTGCAATTTGT
 224 ttatactctccgggtctgccgtgcgcgtaatgaaagacgtctgacaggtt   1174 CTGTGAAGACAGAAGCTTTTATTTCAgtaagtttcaaagcattacnagtt
 274 tatagcggtgttgtcttggttttataagtaggaaaaccagttcgggttct   1224 tccccaatggctgcgtgattgctcatttgcctgttgaatctctctgttgt
 324 gtagatgcagtgctcgcatcagttttgtgcagtatgagcccccgggacatc   1274 gcccttgcacacatctgtttggagcaaaagtgggaagttacccactacna
                                                        1324 atacttcgttactgtactccagtatagttttcagttagaatttttgcccc
                                                        1374 ctacatttttaaacagatatctgtacttctactcc
```

FIG. 3B

IGF-I

IGF-I

IGF-II

IGF-II

FISH INSULIN-LIKE GROWTH FACTOR II PROMOTER

FIELD OF THE INVENTION

This invention (published in *DNA and Cell Biology* (1998), 17:359–376, and *Bioindustry* (1998), 9:1–9, hereinafter incorporated by reference) relates to the findings of the DNA sequences of fish insulin-like growth factor II (IGF-II) promoter regions and recombinant IGF-II promoters and the expression of said IGF-II promoter regions and recombinant IGF-II promoters in eukaryotic cells and fish embryos of another fish species. The integration of said IGF-II promoter regions and recombinant IGF-II promoters into the somatic and germ cells of fish from another species results in the creation of a transgenic fish. The results of this invention demonstrate that fish IGF-II promoter regions and recombinant IGF-II promoters not only are acting as a growth factor which can stimulate the growth and development of fish, but also are capable of being expressed in eukaryotic cells other than fish, such as in human lung large cell carcinoma cells.

BACKGROUND OF THE INVENTION

Insulin-like growth factors (IGFs) are mitogenic peptide hormones. There are two kinds of IGFs, namely, IGF-I and IGF-II. These two polypeptides have high homology of protein folding structure and play important regulatory roles in growth and differentiation of vertebrates.

The gene structure of IGF-I has been reported in mammals (e.g., humans, rats, sheep) and fish (e.g., salmon). The mature form of the IGF-1 peptide is a 70 amino acid polypeptide which mediates the growth-promoting actions of growth hormone as well as having important local paracrine and autocrine roles in multiple organs (Kavsan et al. (1993), *DNA and Cell Biology*, 12:729–737).

The gene structure of IGF-II has been analyzed in various mammals including humans. Until recently, there has been no report relating to the gene structure of IGF-II in fish. The inventors of the present invention are the first to have discovered the IGF-II gene structure in fish (Chen et al., *DNA and Cell Biology* (1997), 16:883–892). Their findings demonstrate that the gene structure of fish IGF-II is different from that in mammals. For example, human IGF-II gene consists of 10 exons about 30 kb in length, which encode a mature, circulating polypeptide approximately 70 amino acids in length (Gray et al. (1987), *DNA*, 6:283–295). In contrast, the mature form of fish IGF-II polypeptide is contained in 4 exons about 13 kb in length, although it is also approximately 70 amino acids in length (Chen et al., *DNA and Cell Biology* (1997), supra).

The mature form of IGF-II polypeptide in different fish species is highly conserved, suggesting that an IGF-II polypeptide derived from one fish species may display similar growth promotion effects on another fish species.

Although IGF-I and IGF-II share high homology of protein folding structure and similar growth promotion effects, their biologic effects are mediated by different IGF receptors. The IGF-I receptor is a tyrosine kinase receptor; the IGF-II receptor is a mannose-6-phosphate receptor.

Recently, studies regarding the findings of fish IGF-I promoters have been reported by several groups of investigators (Koval et al. (1994), *DNA and Cell Biology*, 13:1057–1062; Kulik et al. (1995), *J. Biol. Chem.*, 270:1068–1073). These reports show that the IGF-I promoters have potent stimulatory activity in cells, suggesting that the IGF-I promoters may play a regulatory role in stimulating the expression of IGF-I in cells or tissues by providing cells or tissues with transcription factor binding, especially of the liver-specific transcription factor.

So far, no study, other than the one to be presented by the inventors in the present invention, has been reported concerning the IGF-II promoter region(s) in fish.

In the invention to be presented below, the inventors will describe their findings of the DNA sequences of the IGF-II promoters in fish. Because these inventors also have completed substantial research on the IGF-I promoters and because IGF-I and IGF-II have been regarded as possessing similar regulatory functions, the inventors will present their findings of IGF-I promoters together with those of IGF-II promoters in the following sections, particularly for comparison purpose. These inventors will show that fish IGF-II promoters not only affect the growth of fish embryos earlier than IGF-I promoters but also display higher levels of gene expression than IGF-I promoters. The inventors will also show that an IGF-II promoter from one fish species not only can be expressed in eukaryotic cells other than fish, such as human cells, but also can be integrated into the somatic and germ cells of another fish species, thus creating a transgenic fish.

SUMMARY OF THE INVENTION

The present invention includes the following findings: (1) identification and characterization of the promoter regions of fish IGF-II gene (there are two IGF-II promoter regions upstream from the IGF-II gene, namely, the first and the second IGF-II promoter regions); (2) determination of the promoter activity in different segment or segments of the IGF-II promoter regions (hereinafter referred to as "the recombinant IGF-II promoters") by inserting said recombinant IGF-II promoter segment(s) into a vector to form a plasmid construct and transfecting said plasmid construct into eukaryotic cell lines; (3) expression of fish IGF-II promoter regions or recombinant IGF-II promoters in eukaryotic cell lines; and (4) expression of fish IGF-II promoter regions or recombinant IGF-II promoters in fish embryos of another species, thus, creating a transgenic fish.

There are two promoter regions in IGF-II gene which have demonstrated promoter activities, namely, the first and the second IGF-II promoter regions. The first promoter region has the DNA sequence of SEQ ID NO:1, and the second promoter region has the DNA sequence of SEQ ID NO:13.

Relatively high promoter activities have been found in some segments of the two IGF-II promoter regions. For instance, the first IGF-II promoter region comprises several segments which, individually or in combination of several segments, have shown promoter activities. These segments, which collectively called "the recombinant IGF-II promoters", have the DNA sequences of SEQ ID NO:2, SEQ ID NO:3, SEQ ID NO:4, SEQ ID NO:5, and SEQ ID NO:6. The preferable recombinant IGF-II promoters (i.e., showing high promoter activities) include a segment having DNA sequence of SEQ ID NO:6 and segments containing DNA sequences of SEQ ID NO:4, SEQ ID NO:5, and SEQ ID NO:6.

In order to detect the promoter activity and mass produce IGF-II promoter region and recombinant IGF-II promoters, 6 synthetic primers are designed. These 6 primers have the DNA sequences of SEQ ID NO:7, SEQ ID NO:8, SEQ ID NO:9, SEQ ID NO:10, SEQ ID NO:11, and SEQ ID NO:12.

To test the promoter activity of either a fish IGF-II promoter region and a recombinant IGF-II promoter in eukaryotic cells, the IGF-II promoter region or recombinant IGF-II promoter is first amplified by polymerase chain reaction (PCR) method using the above mentioned 6 synthetic IGF-II primers; the amplified promoter sequence is ligated with a chloramphenicol acetyltransferase (CAT) coding sequence, and then inserted into a vector to form a plasmid construct; the plasmid construct is transfected into human lung large cell carcinoma cells. The relative promoter activity is measured by CAT assay.

The expression of a fish IGF-II promoter region or a recombinant IGF-II promoter in eukaryotic cells is carried out by ligating the IGF-II promoter region and recombinant IGF-II promoter with an IGFs promoter-driven green fluorescent protein (GFP) and a vector to form a plasmid construct. Said plasmid construct is then transfected an eukaryotic cells. The promoter expression is determined by monitoring the fluorescence under a fluorescence microscope or by RT (reverse transcription)—PCR. At least three kinds of eukaryotic cells, including tilapia ovary TO-2 cells, chinook salmon embryo CHSE-214 cells, and human lung large cell carcinoma cells are used for this study.

The expression of a fish IGF-II promoter region and a recombinant IGF-II promoter during fish embryonic development is carried out by creating a plasmid construct containing (1) a fish IGF-II promoter region or a recombinant IGF-II promoter, (2) a GFP coding sequence, and (3) a vector. This plasmid construct is intracytoplasmically injected into a fertilized fish egg from a species other than the one producing the fish IGF-II promoter region or recombinant IGF-II promoter. For example, a zebrafish (Brachydanio rerio) embryo has been employed to be the host for the IGF-II promoter region or recombinant IGF-II promoter extracted from tilapia. By monitoring the fluorescence development during fish embryonic development, it is evident that the IGF-II promoter region or recombinant IGF-II promoter has been integrated into the somatic cells and germ cells, especially in eye, muscle, corpuscle, floor plate, horizontal myoseptum, yolk sac extension, and yolk sac, thus, providing supports that a transgenic fish which contains and expresses another fish species' IGF-II promoter gene is created thereof.

BRIEF DESCRIPTION OF THE DRAWINGS

FIG. 1 shows PCR primers which are designed to study the (1) cloning of IGF-I cDNA (IGF-I primers 1 and 2); (2) cloning of IGF-I genomic DNA (IGF-I exon primers 1–6); (3) 5' rapid amplification of cDNA ends (5'RACE) (IGF-I GSP 1 and IGF-II GSP 1); (4) IGF-I promoters (IGF-I P2–P7); (5) IGF-II promoters (IGF-P3–P9 and P11); and (6) checking the expression of IGFs promoter-driven green fluorescent protein (GFP) (GFP 1 and GFP 2). W=A or T; Y=C or T; K=G or T; S=C or G; M=A or C; R=A or G.

FIG. 2 shows a partial nucleotide sequence of IGF-I genomic DNA isolated from tilapia (Oreochromis mossambicus). Tilapia IGF-1 exon sequences and 5' flanking sequences are shown in uppercase letters; intronic sequences are shown in lowercase letters. #=stop codon; *=start codon. Numbered arrows under sequence indicate positions for chloramphenicol acetyltransferase (CAT) transient transfected expression assays of PCR-constructed primer. Regions of 5'RACE (rapid amplification of cDNA 5' ends) termini are marked by arrows above sequence and labeled 5'RACE.

FIG. 3 shows the nucleotide sequence of promoter region of tilapia (Oreochromis mossambicus) IGF-II gene. Numbered arrows under sequence indicate positions for chloramphenicol acetyltransferase (CAT) assay of PCR-constructed primer. Regions of cDNA 5' end as determined by 5'-RACE (rapid amplification of cDNA 5' end) are remarked by arrows. Exon sequences and 5' flanking sequences are shown in uppercase letters; intron sequences are shown in lowercase letters. Translation initiation codon is underlined and marked.

DESCRIPTION OF THE PREFERRED EMBODIMENTS

Figure 4A:
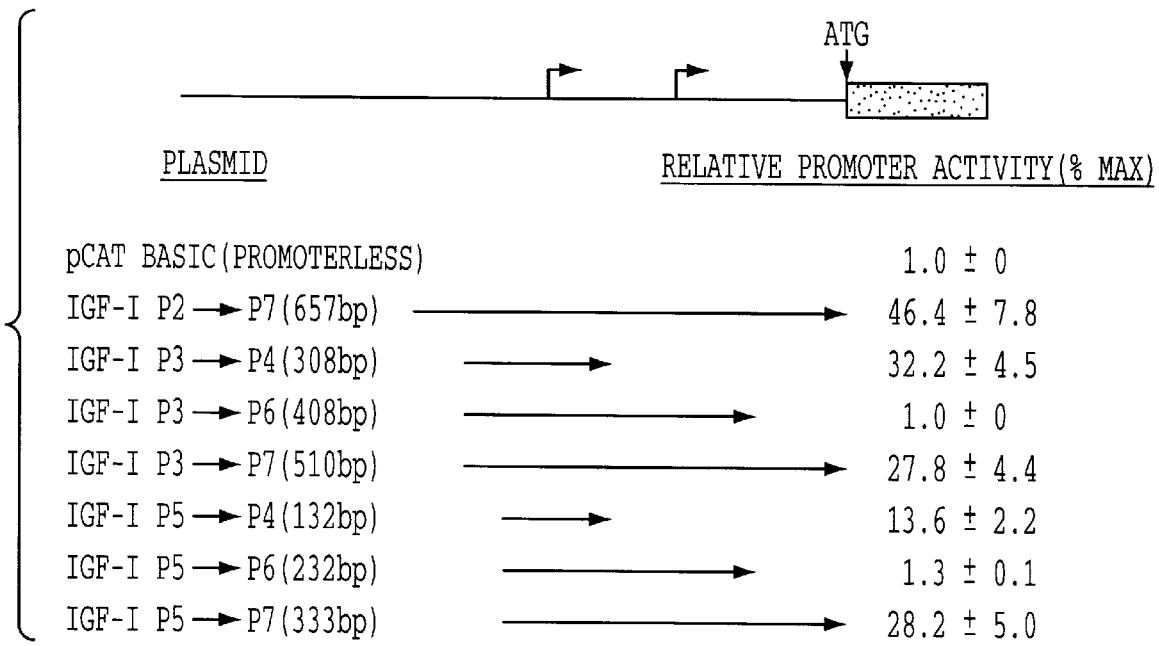
FIGS. 4A–4B show the promoter activity in 5' flanking region of tilapia (Oreochromis mossambicus) IGF-I and IGF-II genes. The IGF-CAT fusion plasmids containing fragments of 5' flanking region were transfected into human lung large cell carcinoma, and CAT activity was measured 48 hrs later. All transfections were performed in triplicate. Values (mean±SEM) represent CAT activity relative to that in cells transfected with promoterless plasmid pCAT-basic vector, defined as 1.0.

This invention discloses four embodiments, which are: (1) DNA sequence analysis of fish IGF-I and IGF-II promoter regions; (2) determination of the relative promoter activity in the recombinant IGF-II promoters; (3) expression of an IGF-II promoter region or a recombinant IGF-II promoter in eukaryotic cells; and (4) creation of a transgenic fish by intracytoplasmically injecting the IGF-II promoter regions or the recombinant IGF-II promoters in said fish embryos. The following descriptions of the embodiments are constructed in a way that the experimental procedures are listed as EXPERIMENTS following each embodiment, and the findings based upon the experimental designs shown in the embodiment are listed as EXAMPLES. One fish species, i.e., tilapia, is chosen for illustration purpose. Other fish species, such as carp, salmon, catfish and rainbow trout, have also been investigated by the inventors of the present invention which show similar results as those in tilapia.

EMBODIMENT 1: DNA Sequences of Fish IGF-I and IGF-II Promoter Regions

The first embodiment of the present invention relates to findings of the DNA sequences of the promoter regions in fish IGF-I and IGF-II genes. This embodiment is accomplished by the establishment of the following experimental procedures:

EXPERIMENT 1. Isolation and Characterization of Fish IGF-I cDNA.

Fish IGF-I cDNA was obtained by reverse transcription of fish total RNA. In order to obtain high levels of IGF RNA, the fish were injected at 8 hrs intervals with yellowfin porgy (*Acanthopagrus latus*) growth hormone (GH) at a dose of 1 μg/g of body weight for three doses. Total liver RNA was prepared according to the manufacturer's protocols (UL-TRASPEC™—II RNA isolation system; Biotecx Laboratories, Inc., U.S.A.).

The first-strand of cDNA was generated from 30 μg of total RNA in a 37 μl reaction volume by adding IGF-I primers 1 and 2 (FIG. 1, for discussion, please see EXAMPLE 1). Briefly, the mixture was incubated at 80° C. for 10 minutes, and allowed to cool down slowly to room temperature in order to anneal the IGF primers to the corresponding cDNA. This mixture was further mixed with 5 μl of 10 X first-strand buffer (Stratagene), 2 μl of 100 mm dNTPs (Strategene), and 2 μl of SuperScript™ II RNase H⁻ reverse transcriptase (200 U/μl; GIBCO BRL) and incubated at 42° C. for 60 minutes which followed by additional incubation at 95° C. for 5 minutes. After incubation, the reaction vessel was immediately placed on ice.

The PCR reaction was carried out in a final volume of 100 μl. The reaction sample contained the first-strand cDNA, 10 μl of 10 X PCR buffer (HT Biotechnology), 200 μM of each dNTP, 1 μg of IGF primers, and 2.5 units of Taq DNA polymerase. The reaction mixture was subjected to 35 PCR cycles of 1 minute at 94° C. (denaturation), 2 minutes at 42° C. (annealing), and 2 minutes at 72° C. (extension); the PCR products were then resolved on 2% agarose gel.

The PCR products were size-separated by gel electrophoresis and digested with EcoRI. The digested product of the predicted size (551 bps) was then subcloned into the pUC18 plasmid using 5 U of T4 DNA ligase. The recombinant plasmid was transferred into the *E. coli* JM109 strain. The nucleotide sequences of each insert were determined by the dideoxynucleotide chain termination method using forward and reverse primers. The predicted IGF-I nucleic acid sequences were performed using the Genetics Computer Group Gap program.

EXPERIMENT 2. Isolation of Fish IGF-II Genomic Clones.

Fish IGF-II genomic clones were isolated by screening approximately 1 million recombinant bacteriophages from the fish genomic library using a hybridization method with the $^{32}$P-labeled fish IGF-II cDNA fragments in a hybridization buffer (containing SDS [7 g/100 ml], 0.5 M EDTA (pH 8.0) [100 μl/100 ml], 50% PEG8000 [20 ml/100 ml], 40% formamide [40 ml/100 ml]) at 42° C. for 16 hrs. The S domain to E domain region of *Acanthopagrus schlegeli* IGF-I cDNA is used as the hybridization probe according to the inventors' previous report (Chen et al., *DNA and Cell Biology* (1997), supra). The positive plaques were purified. DNA restriction mapping of these positive plaques was further conducted by southern blotting using $^{32}$P-labeled fish IGF-II cDNA probes.

EXPERIMENT 3. DNA Sequence Analysis.

To analyze the gene structure and promoter region of fish IGF-II genomic DNA, the IGF-II phage DNAs were digested with SacI restriction enzyme, then subcloned into the pBluescript vector and transformed into XL1 Blue *E. coli* host cells. The DNA sequence of the IGF-II genomic clones was determined using the QIAGEN plasmid extraction kit to extract DNA. One strand of DNA was sequenced by an ABI autosequencer. The nucleic acid sequences were compared with all published sequences on the Genetics Computer Group computer program.

EXPERIMENT 4. Rapid Amplification of 5' cDNA ends (5'RACE).

To determine the location of the transcription start site, a method which determines the 5' cDNA terminus (hereinafter called "5'RACE") was designed. This method employed two primers (namely, IGF-I GSP1 [SEQ ID NO:22] and IGF-II GSP1 [SEQ ID NO:23]). The nucleotide sequences of these two primers are shown in FIG. 1.

The 5'RACE procedure strictly followed the instruction manual of Life Technologies, U.S.A. Briefly, a sample containing (a) IGFs genomic or cDNA, and (b) IGF-I GSP1 [SEQ ID NO:22] or IGF-II GSP1 [SEQ ID NO:23] primer is subjected to polymerase chain reaction (PCR) reaction. After PCR, the 5'RACE products were analyzed on a 1.5% agarose gel transferred to nylon membranes (BioRad, U.S.A.), where a hybridization procedure using IGF genomic DNA or cDNA was employed. After verifying which fragments hybridized with the probe, restriction endonuclease-digested 5'RACE products were cloned into the pBluescript plasmid vector (Strategene) and sequenced to confirm the DNA sequence.

RESULTS:

EXAMPLE 1

PCR Primers Designed For IGF-Promoters, 5'RACE, and GFP assays.

As shown in FIG. 1, a total of 26 primers were designed and synthesized for (1) IGF-I cDNA cloning (2 primers—IGF-I primers 1 and 2 [SEQ ID NO:14–15]); (2) IGF-I genomic DNA cloning (6 primers—IGF-I exon primers 1–6 [SEQ ID NO:16–21]); (3) first-strand cDNA synthesis of 5'RACE (2 primers—IGF-I GSP 1 (SEQ ID NO:22) and IGF-I GSP 2 (SEQ ID NO:23)); (4) IGF-I promoter assay (6 primers—IGF-I P2–P7 [SEQ ID NO:24–29]); (5) IGF-II promoter assay (7 primers—IGF-P3–P9 [SEQ ID NO. 30–31 and 7–11] and P11 [SEQ ID NO.12]); and (6) GFP expression determination (2 primers—GFP 1 (SEQ ID NO:32) and GFP 2 (SEQ ID NO:33)).

IGF-I primers 1 and 2 are universal primers for fish. The 5' end of these primers contains the EcoRI restriction site. These two primers were used to assist reverse transcription of the first strand of cDNA generated from fish total RNA by SuperScript™ RNase H⁻ reverse transcriptase (GIBCO BRL, U.S.A.) and PCR.

IGF-I exon primers 1–6 are used to produce IGF-I genomic DNA fragments for DNA sequence analysis.

5'RACE is designed to locate the transcription start site of IGF-I and IGF-II. The 5'RACE procedure requires two primers IGF-I GSP1 (for IGF-I gene) and IGF-II GSP1 (for IGF-II gene).

IGF-I P2–P7 (SEQ ID NO:24–29) and IGF-II P3–P9 and P11 (SEQ ID NO:30–31, and 7–12) are primers specially designed to study promoter activities of IGF-I (i.e., using primers IGF-I P2–P7 [SEQ ID NO:24–29]) and IGF-II (i.e., using IGF-II P3–P9 and P11 [SEQ ID NO:30–31 and 7–12]).

GFP (green fluorescent protein) (for further discussion, please see embodiment 3, infra) is an IGF-promoter-driven protein which displays green fluorescence under fluorescence microscope. Primers GFP 1 (SEQ ID NO:22) and GFP 2 (SEQ ID NO:23) were used to assist in amplification of the GFP coding region and for reverse transcription of GFP mRNA.

EXAMPLE 2
DNA Sequence of the Promoter Area of Tilapia IGFs Gene.

The DNA sequences of the promoter regions of IGF-I and IGF-II gene in tilapia are shown in FIGS. 2 and 3. The promoter regions of both the IGF-I and IGF-II genes were located in Exon 1. The IGF-II promoter DNA sequence shown in FIG. 1 covered the DNA sequence of about 5.7 kb 5' upstream of the first methionine sequence containing the tilapia IGF-II promoter. Within this promoter area, there were two regions which showed promoter activity, namely, the first and the second IGF-II promoter regions.

In the first IGF-II promoter regions, a TATA-like sequence (underlined) was found between –32 bp and –26 bp. Also, a Sp1-like binding sequence was found between –292 bp and –285 bp.

The second IGF-II promoter region was located between –5477 bp and –4477 bp. In this region, there were one DBP-binding sequence, one GHF-1 finding sequence, one AR-binding sequence, and one HNF (hepatocyte nuclear factor)-5-binding sequence.

Unlike the IGF-II promoters, IGF-I promoter segments were located upstream and downstream of the transcription start codon (as shown by 5'RACE termini in FIG. 2). A TATA-like consensus sequence was found about 300 bp upstream of the first methionine. A possible HNF-5-binding sequence, one possible HNF-1-binding sequence, and one possible AP-1-binding sequence were also found in the IGF-I promoter region.

EMBODIMENT 2: Determination of Promoter Activity in Recombinant IGF-I and IGF-II Promoters The second embodiment of this invention is to determine the relative promoter activity in segment(s) of fish IGF-I and IGF-II promoter regions. This was accomplished by first amplifying a DNA sequence (i.e., a recombinant IGF-I or IGF-II promoter) corresponding to a segment or segments of either an IGF-I or an IGF-II promoter region using PCR method. An IGF-I primer (e.g., an IGF-I P2 [SEQ ID NO:24], P3[SEQ ID NO:25], P4[SEQ ID NO:26], P5[SEQ ID NO:27], P6[SEQ ID NO:28], or P7 [SEQ ID NO:29] or an IGF-2 primer (i.e., IGF-II P3[SEQ ID NO:30], P4[SEQ ID NO:31], P5[SEQ ID NO:7], P6[SEQ ID NO:8], P7[SEQ ID NO:9], P8 [SEQ ID NO:10], P9[SEQ ID NO:11], or P11 [SEQ ID NO:12] was used to designate a particular recombinant IGF-I or IGF-II promoter.

The amplified recombinant IGF-I or IGF-II promoter was then ligated with a chloramphenicol acetyltransferase (CAT) coding region, which was then inserted into a promoterless vector to form a plasmid construct. The constructed plasmid construct was then transfected into a cell line such as human lung large cell carcinoma cells. The relative promoter activity was determined by measuring the CAT activity and comparing the CAT activity with that in the entire IGF-II promoter region.

The CAT transient transfected expression assay procedure is described as follows:

EXPERIMENT 5. Chloramphenicol Acetyltransferase (CAT) Transient Transfected Expression Assay.

A CAT transient transfected expression assay procedure is employed to determine the relative promoter activity in a recombinant IGF-II promoter. This assay procedure was conducted as follows: First, an approximately 2 kb of SacI-SacI fragment containing the 5' flanking region of the IGF-II gene was obtained from an IGF-II genomic clone.

Second, the fragment was amplified by PCR method using a specific IGF-II primer (which was selected from the group consisting of primers P2, P3, P4, P5, P6, P7, P8, P9 and P11) (See FIG. 1). The location of the interacting point of each primer is depicted in FIG. 3.

Third, the PCR product was digested with PstI and HindIII restriction endonucleases, and the fragment was ligated into the HindIII and PstI sites of a pCAT-Basic vector (Promega, U.S.A.) to form a plasmid construct containing a CAT coding region. The pCAT-Basic vector is a promoterless plasmid containing multiple cloning sites upstream of a CAT cDNA.

Finally, the plasmid construct was transfected into human lung large cell carcinoma cells. The CAT activity was measured 48 hrs after transfection.

RESULTS:

EXAMPLE 3
Relative Promoter Activity in Recombinant IGF-I or IGF-II Promoter.

To determine which segment(s) of the IGF-I or IGF-II promoter regions are involved in its regulation, a recombinant IGF-I or IGF-II promoter was constructed. For IGF-I promoter region, seven plasmid constructs, which contained PCR products of recombinant IGF-I promoters of IGF-I P2→P7 (657 bp), IGF-I P3→P4 (308 bp), IGF-I P3→P6 (408 bp), IGF-I P3→P7 (510 bp), IGF-I P4←P5 (132 bp), IGF-I P5→P6 (232 bp), and IGF-I P5→P7 (333 bp), were selected.

For the first IGF-II promoter region, eight plasmid constructs, which contained PCR products of recombinant IGF-II promoters of IGF-II P3→P11 (600 bp), IGF-II P4→P11 (550 bp), IGF-II P5→P11 (450 bp), IGF-II P6→P11 (400 bp), IGF-II P7→P11 (350 bp), IGF-II P9→P11 (250 bp), IGF-II P7←P11 (350 bp), and IGF-II P8←P11 (300 bp), were selected.

Each of these recombinant IGF-I or IGF-II promoter was ligated with a CAT coding sequence and inserted into a vector to form a plasmid construct. The plasmid construct was then transfected into a human lung large cell carcinoma cell line. The relative promoter activity of the individual recombinant IGF-I or IGF-II promoter was determined by CAT assay.

As shown in FIG. 4(A), the recombinant IGF-I promoter corresponding to segment of IGF-I P2→P7 (46.4±7.8) contained the maximal IGF-I promoter activity. Deletion of the segments of IGF-I P2, P3 and P4 from the recombinant IGF-I P2→P7 (resulting in creating a recombinant IGF-I promoter containing IGF-I P5→P7) decreased the CAT activity. In contrast, IGF-I P3→P6 and IGF P5→P6 contained the minimal activity, which were 1.0±0 and 1.3±0.1, respectivity. The activities of the rest of the recombinant IGF-I promoters included 32.2±4.5 for IGF-I P3→P4, 27.8±4.4 for IGF-I P3→P7, 28.2±5.0 for IGF-I P5→P7, and 13.6±2.2 for inverted segment IGF-I P4←P5. These results show that the segments of P4 to P6 contains a positive regulatory element. Also, the region downstream of the transcription start site and the sequence of about 120 bp from P6 to P7 may contain a negative regulatory element, which gives rise to decrease in CAT activity.

Figure 4B:
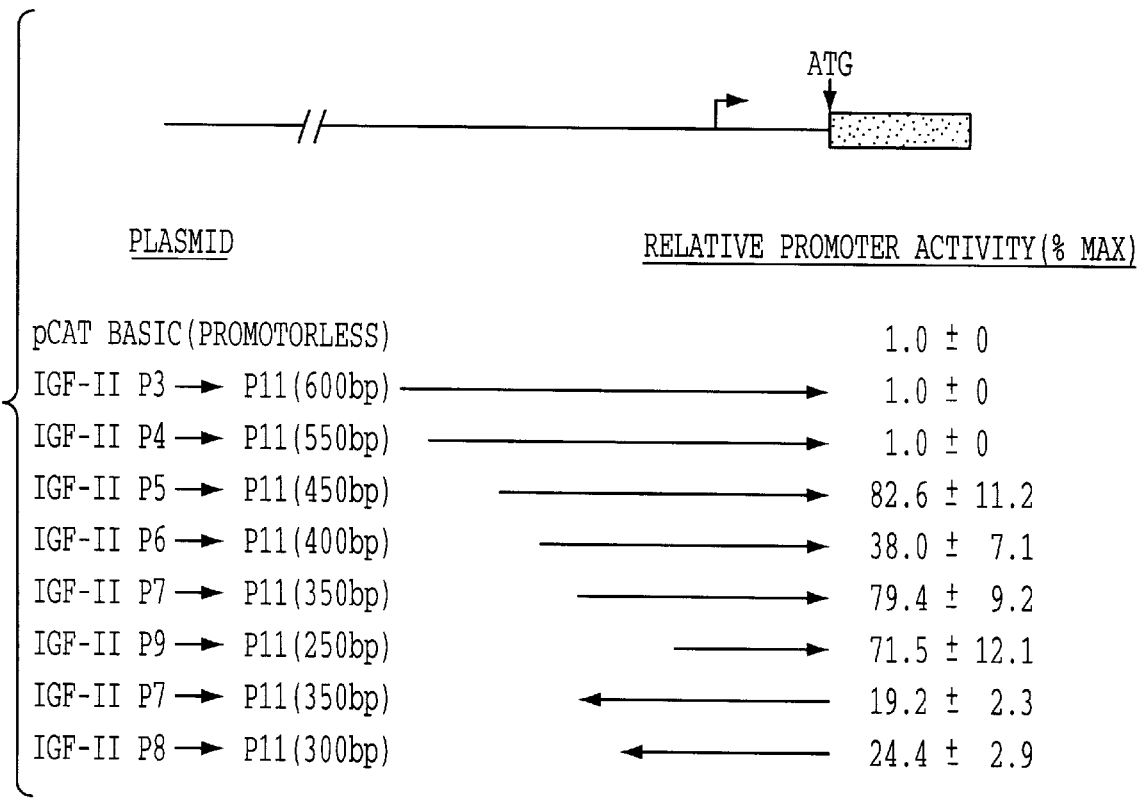
Figure 5A:
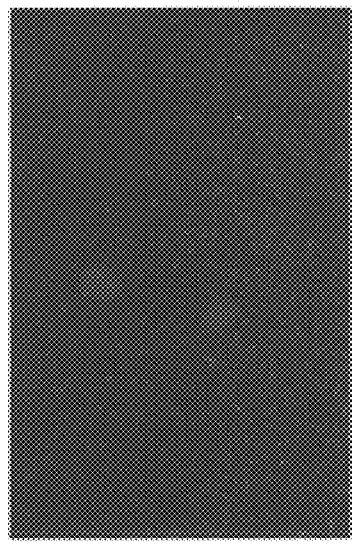
FIG. 5 shows human lung large cell carcinoma cells transiently transfected with (A) an IGF-I promoter, and (B) an IGF-II promoter. The IGFs promoter is ligated to pEGFP-1 vector and expressing GFP. Fluorescence image (left) and bright-field photograph (right).
Figure 5B:
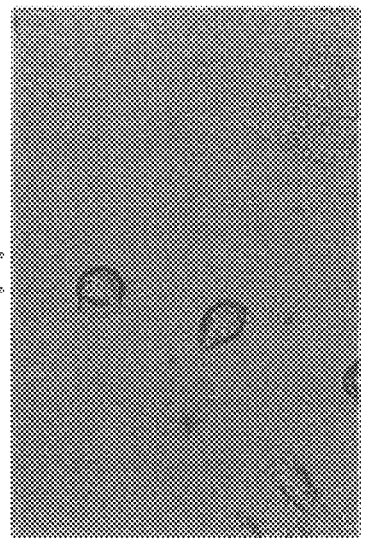
Figure 5C:
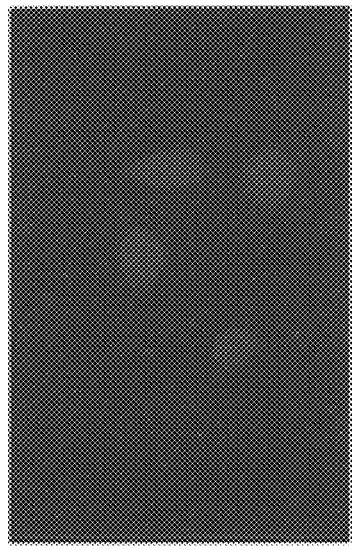
Figure 5D:
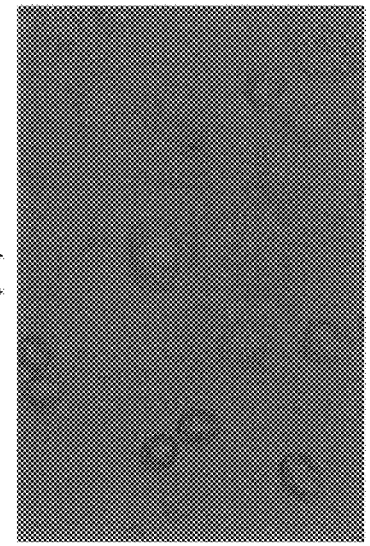

FIG. 4(B) shows that the recombinant IGF-II promoter corresponding to IGF-II P5→P11 contained the highest CAT activity (82.6±11.2), as compared to the rest of the recombinant IGF-II promoters tested in FIG. 4. Deletion of the segment P5 (SEQ ID NO:2) from IGF-II P5→P11 to IGF-II P6→P11 rapidly decreased CAT activity to 38±7.1. However, further deletion of the segment P6 (SEQ ID NO:3) from IGF-II P6→P11 to IGF-II P7→P11, and the segment P7 (SEQ ID NO:4) from IGF-II P7→P11 to IGF-II P8→P11 sharply increased CAT activity to 79.4±9.2 and 71.5±12.1, respectively. Also, inverted orientation of the recombinant IGF-II promoter produced lower promoter activity than was seen with forward orientation (for example, IGF-II P7←P11 had CAT activity of 19.2±2.3; and IGF-II P8←P11 had CAT activity of 24.4±2.9). Because IGF-II P5 (SEQ ID NO:2) contained a Sp1-binding regulatory element, it is possible that this Sp1 element plays an important role in regulating the IGF-II promoter function in tilapia.

As for the second IGF-II promoter region, because it contains transcription- and growth hormone-binding-sites as those found in the IGF-I and the first IGF-II promoter region, it is possible that relative promoter activity may exist at different segment(s) of this second IGF-II promoter region.

EMBODIMENT 3: Expression of Fish IGF-II Promoter Activity in Eukaryotic Cells.

The third embodiment of the present invention relates to the expression of IGF-II promoter activity in eukaryotic cells. Three kinds of eukaryotic cells, which include two fish cells (e.g., chinook salmon embryo CHSE-214 cells and tilapia ovary TO-2 cells [established from ovaries of healthy adult tilapia hybrids of *Tilapia mossambica* X *Tilapia nilotica*) and one human cells (e.g., human lung large cell carcinoma cells) were applied to study the expression of a fish IGF-II promoter DNA obtained from one fish species to (1) the same or different fish species, or (2) mammalian cells (e.g., human lung large cell carcinoma cells).

Both tilapia ovary cells (TO-2) and chinook salmon embryo CHSE-214 cells were seeded (3×10$^4$ cells/well) in 24 well-plates containing MEM/F12 medium supplemented with 10% BSA for 24 hrs before transfection. Human lung large cell carcinoma cells (ATCC NCI H1299) were grown in DMEM (glucose 4.5 g/l) containing 10% new-born calf serum. Approximately 6×10$^5$ cells were seeded for 12 hrs. The transfection procedure for the above three cell lines followed the calcium phosphate-mediated DNA transfection protocol. Typically, the transfection lasted for 12 hrs.

The expression of fish IGF-II promoter regions and the recombinant IGF-II promoters in eukaryotic cells was carried out first by ligating an IGFs promoter-driven green fluorescent protein (GFP) coding sequence with the IGF-II promoter regions or recombinant IGF-II promoters. This ligated sequence was then inserted into a vector to form a plasmid construct. The plasmid construct was then transfected into eukaryotic cells. The expression of the IGF-II promoter was monitored under a fluorescence microscope or determined by RT-PCR (reverse transcription of fish embryo RNA followed by PCR amplification).

The preferable vector for forming the plasmid construct for this study is pEGFP-1 (CLONTECH Laboratories, Inc.; the pEGFP-1 vector sequence can be found in GenBank accession number U55761). This vector contains a HindIII-SalI site.

The preparation of the GFP cDNA and the observation of GFP under fluorescence microscope are described as follows:

EXPERIMENT 6. Preparation of GFP cDNA by RT-PCR and Fluorescence Microscope Observation of GFP peptide.

GFP in fish whole embryo or fish total RNA was identified and amplified by PCR method using two primers, namely,
GFP 1 and GFP 2. GFP 1 primer has the DNA sequence of 5'-TTCACCGGGGTGGTGC CCATCCTGGTC (SEQ ID NO:32). GFP 2 primer has the DNA sequence of 5'-TTGAAGAAGA TGGTGCGCTCCTGGACGTAGC (SEQ ID NO:33).

Typically, 1.6 μg of whole embryo or fish total RNA and the GFP 1 and GFP 2 primers were put together in one-tube and used to amplify internal fragments of GFP first-strand cDNA. The PCR was run continuously to amplify about 317 bp of the GFP coding region according to the manufacturer's instructions (AMPLY RT/PCR Kit; LTK BioLaboratories, R. O. C.). The amplification program was conducted in a Perkin-Elmer 2400 thermocycler as follows: 1 cycle of 5 min at 60° C., 30 min at 42° C., 35 cycles of 1 min at 94° C., 2 min at 55° C., and 2 min at 72° C. followed by a final extension of 7 min at 72° C. then immediately stored at 4° C. Each RT-PCR included control groups: one tube contained only GFP 1 and GFP 2 primers, and another tube contained only embryos or fish total RNA mixtures. The PCR amplification products (5 μl of 20 μl) were analyzed on 1.5% agarose gel and transferred to nylon membranes (BioRad, U.S.A.). The ethidium bromide stained band of 310 bps in length corresponded to GFP. The membranes were probed with [$^{32}$P] dCT-radiolabeled GFP cDNA fragments using hybridization procedure shown in Embodiment 1 (supra).

Cells or fish embryos containing GFP peptide can be observed and photographed on an Olympus microscope IX70 and Leica MPS 48/52 dissection microscope with a fluorescence filter using a long-wave UV lamp.

RESULTS

EXAMPLE 4

Expression of IGF-I and IGF-II promoter-GFP in human cells.

FIG. 5 illustrates the expression of fluorescence by GFP peptide in (A) recombinant IGF-I promoter- or (B) recombinant IGF-II promoter-transfected human lung large cell carcinoma cells. The recombinant IGF-I and IGF-II promoters used in FIG. 5(A) and 5(B) were IGF-I P2→P7, and IGF-II P5→P11, both were proven to contain the maximal recombinant promoter activity in its group as demonstrated in Embodiment 2 (supra).

The results show that the recombinant IGF-II promoter produced higher level of GFP than that of the recombinant IGF-I promoter, which was evident by observing the intensity of fluorescence in both cells. Also, the results demonstrate that both the fish IGF-I and IGF-II promoters were capable of being expressed in human cells.

EMBODIMENT 4: Creation of a Transgenic Fish Which Contains an IGF-II Promoter Region or Recombinant IGF-II Promoter of Another Fish Species.

The fourth embodiment of this invention relates to the creation of a transgenic fish which contains a transgene of an IGF-II promoter region or a recombinant IGF-II promoter from another fish species. To demonstrate that the transgene has been integrated and expressed in the host fish, a GFP system was constructed based upon the RT-PCR method described in EXPERIMENT 6 of Embodiment 3.

The experiment was conducted based upon the following procedures:

EXPERIMENT 7. Preparation of Plasmid DNA, Fish Egg Collection, and Microinjection.

To prepare a plasmid construct, the vector pEGFP-1 (CLONTECH Laboratories, Inc., U.S.A.) was constructed by inserting an IGF-1/IGF-II promoter region or a recombinant IGF-I/IGF-II promoter (e.g., an IGF-I P2 P7 as a HindIII-PstI site or an IGF-II P5→P11 segment as a HindIII-SalI site) from the PCR fragment. Plasmid DNA was extracted according to QIAGEN handbook for the plasmid maxi kit (QIAGEN GmbH and QIAGEN Inc.). After purification, the plasmids were precipitated using ethanol and sodium acetate. The DNA pellet was resuspended in ddH$_2$O and stored in −20° C.

The experimental specimens were maintained under standard conditions. Fertilized eggs were collected, and one of the two cells in the embryo was intracytoplasmically injected with an appropriated amount of supercoiled plasmid DNA.

After injection of the supercoiled plasmid DNA into the embryos, eggs were kept in a 28° C. incubator. Embryos were observed and photographed on an Olympus microscope IX70 and Leica MPS 48/52 dissection microscope with a fluorescence filter using a long-wave UV lamp. The fish embryo RNA extraction method was according to the manufacturer's protocols (ULTRASPEC™-II RNA isolation system; Biotecx Inc., U.S.A.).

RESULTS:

EXAMPLE 5

Expression of IGFs promoter transgene in zebrafish embryos.

Figure 6:
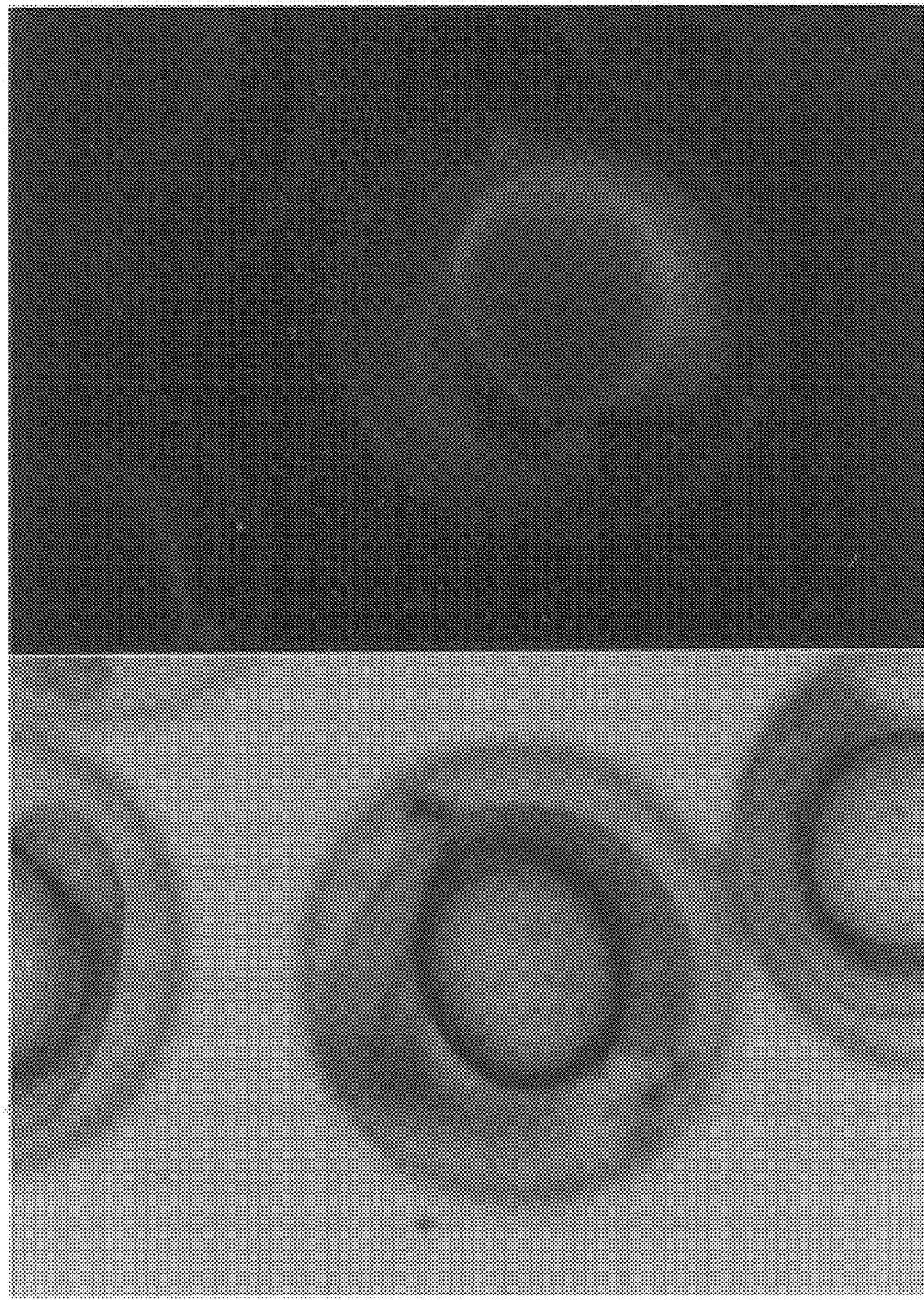
FIG. 6 shows an IGF-I promoter-GFP vector microinjected into zebrafish 2-cell stage fertilized eggs. After 24 hrs of development in freshwater on culture dishes, the GFP was first visibly expressed in whole trunk and head. However, the other embryo which was at the same stage and injected with the same IGF-I promoter-GFP vector shows no GFP. Brightfield photograph (bottom) and fluorescence image (above). All photographs were taken with 45× lens on Olympus microscope IX 70.
Figure 7A:
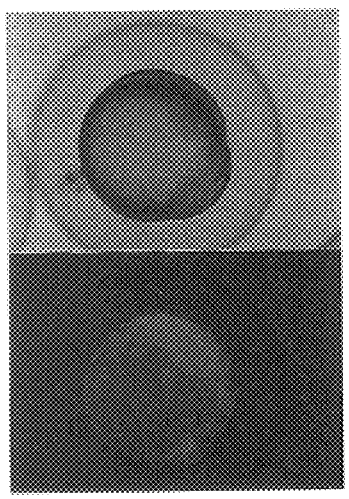
FIGS. 7A–7G show zebrafish 2-cell-stage fertilized eggs which were microinjected with the IGF-II promoter-GFP (green fluorescent protein) vector. Fluorescence (bottom) and brightfield (top) photographs. The GFP was first visibly expressed at 8 hrs (75% epiboly, gastrula period) (A). Photograph was taken with 100× lens on Olympus microscope IX70. The IGF-II promoter-GFP vector was highly expressed from embryo to embryo (B) and from 1 stage to the next (panel C is 24 hrs after injection, and panel D is 48 hrs after injection). Panel D shows too fish of which the upper was not injected. Green fluorescence accumulated in yolk sac, yolk sac extension, and notochord (D). The GFP is visible in horizontal myoseptum (E), eye (F), and floor plate (G) 48 hrs after microinjection.
Figure 7B:
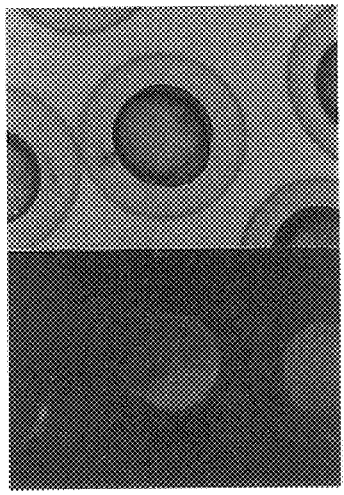
Figure 7C:
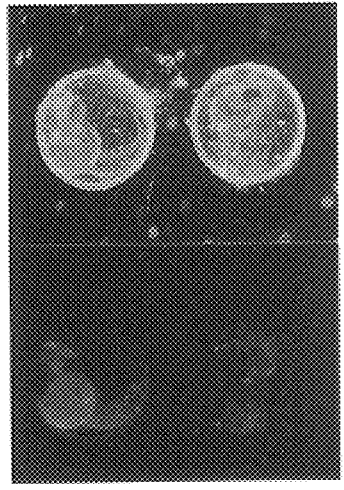
Figure 7D:
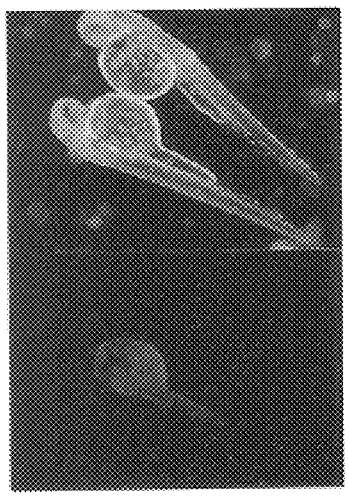
Figure 7E:
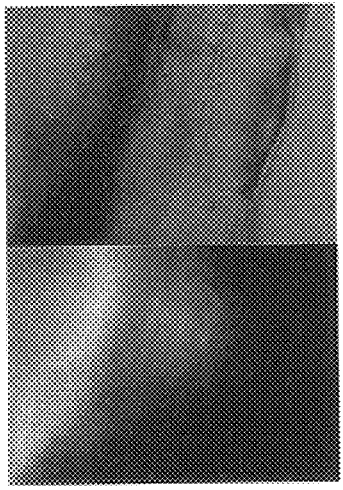
Figure 7F:
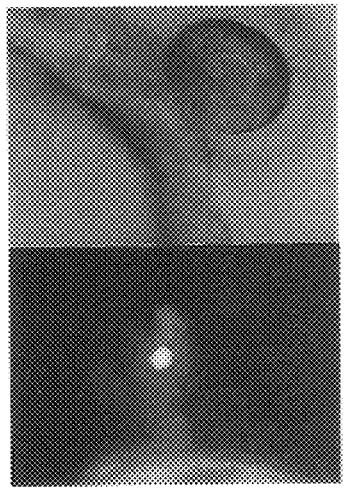
Figure 7G:
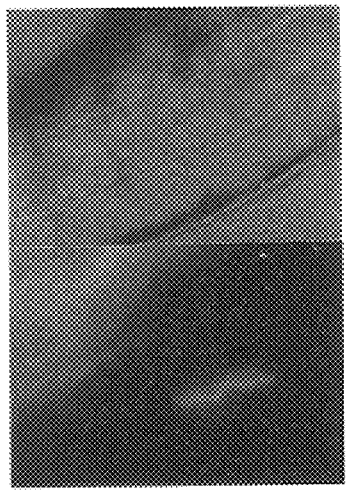

FIG. 6 shows a recombinant IGF-I promoter-GFP vector microinjected into zebrafish 2-cell stage fertilized eggs. The recombinant IGF-I promoter used in this experiment contained an IGF-I P2→P7 segment. About 24 hrs after microinjection, patches of fluorescent cells could be observed in a zebrafish embryo. The low fluorescence in the whole embryo implies that the IGF-I promoter has little expression during the zebrafish straightening period.

FIG. 7 shows zebrafish 2-cell-stage fertilized eggs which were microinjected with the IGF-II promoter-GFP vector. After 8 hrs of microinjection, patches of fluorescent cells were observed in 42 of the 60 embryos (FIG. 7A). These fluorescent cells were visible from embryo to embryo (FIG. 7B) and from one stage to the next (FIGS. 7C and D). In 24 hrs, the fluorescence was visible in the horizontal myoseptum and the eye (FIGS. 7E and F). In 48 hrs, the fluorescence appeared in the yolk sac (FIG. 7D) and floor plate (FIG. 7G). The fluorescence from the segmentation period to the straightening period also appeared in the heart and blood cells. The fluorescence was visible for up to 1 wk.

Figure 8:
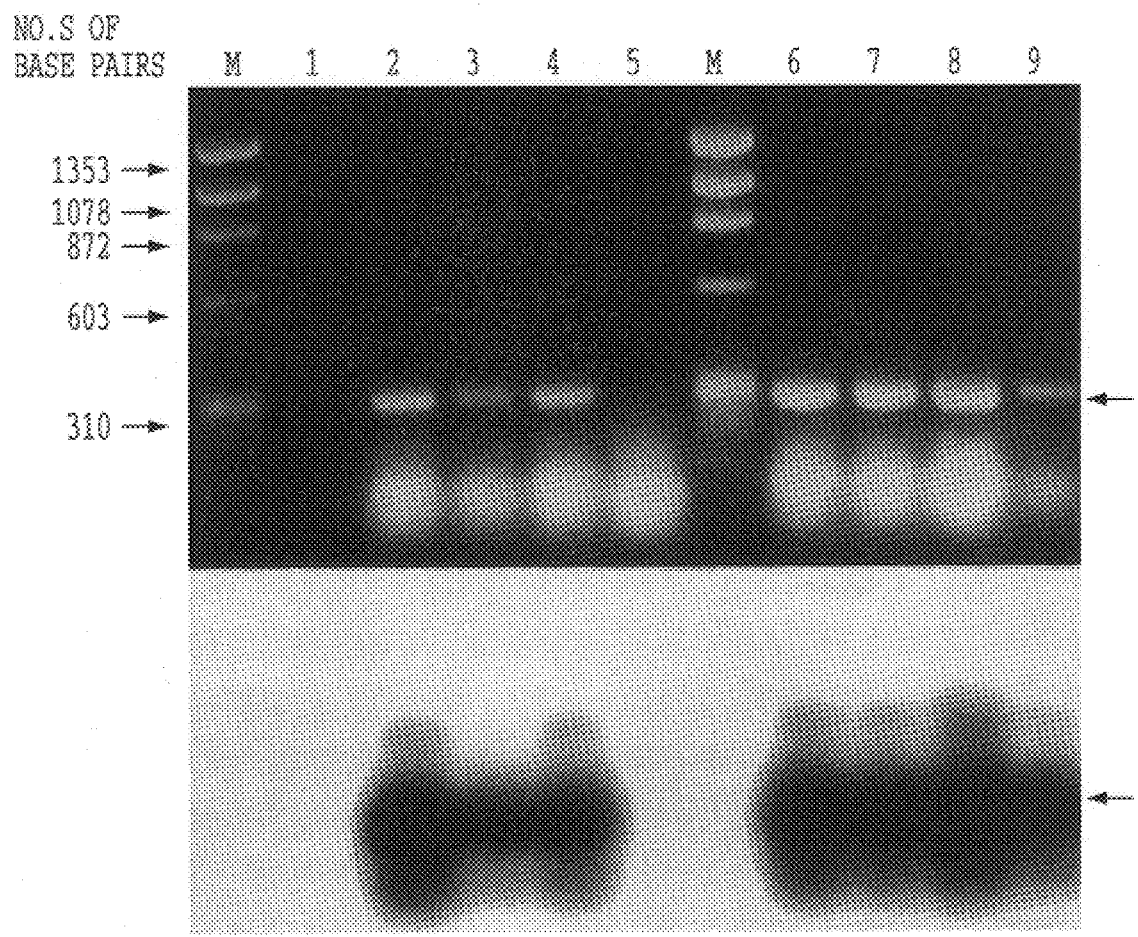
FIG. 8 shows the detection of GFP cDNA in various stage of zebra fish (Brachydanio rerio) (IGF-I: lane 1 to lane 5; IGF-II: lane 6 to lane 9). GFP cDNA is produced from mRNA by RT (reverse transcription)-PCR method. Whole-embryo total RNA and juvenile tilapia total RNA were extracted, and RT-PCR and Southern blot analyses were conducted. Upper picture shows ethidium bromide staining of RT-PCR products using GFP-specific primers (i.e., GFP1 and GFP2, which are shown in FIG. 1). Lower picture shows Southern blot analysis of the gel using $^{32}$P-labeled GFP full-length cDNA as a probe. Lane M is φX174 HaeIII marker. Lanes 1 and 6: 32-cell stage; lanes 2 and 7: 1-K-cell stage; lanes 3 and 8: 30% epiboly stage; lane 4: gastrula stage; lane 5: 1-wk-old fish; lane 9: 2-wk-old fish.

GFP can also be detected according to the RT-PCR method described in EXPERIMENT 6 (supra). RT-PCR was run using primers GFP1 and GFP2 (FIG. 1), followed by Southern blotting and by hybridization assay. The results show that for IGF-I promoter, GFP cDNA was first detected in 1-K-cell period, and after 1 wk, GFP cDNA RT-PCR product could no longer be detected (FIG. 8:lanes 1–5).

For IGF-II promoter, GFP cDNA first appeared at the 32-cell period. After 2 wks of injection, the RT-PCR still continued to be detected (FIG. 8: lane 9), even though the expression was weak.

What is claimed is:

1. A fish first insulin-like growth factor II (IGF-II) promoter region comprising an IGF-II promoter having the DNA sequence of SEQ ID NO:1.

2. A recombinant fish IGF-II promoter comprising an IGF-II promoter fragment, wherein said IGF-II promoter fragment has the DNA sequence which is selected from at least one of the group consisting of SEQ ID NO:2, SEQ ID NO:3, SEQ ID NO:4, SEQ ID NO:5, and SEQ ID NO:6.

3. The recombinant fish IGF-II promoter according to claim 2, wherein said oligonucleotide comprises the DNA sequence of SEQ ID NO:6.

4. The recombinant fish IGF-II promoter according to claim 2, wherein said oligonucleotide comprises SEQ ID NO:4., SEQ ID NO:5, and SEQ ID NO:6.

5. A primer for amplifying a recombinant fish IGF-II promoter according to claim 2, wherein said primer is selected from the group consisting of SEQ ID NO:7, SEQ ID NO:8, SEQ ID NO:9, SEQ ID NO:10, SEQ ID NO:11, and SEQ ID NO:12.

6. A method for making fish IGF-II promoter plasmid construct comprising the step of:
obtaining the IGF-II promoter according to claim 1, amplifying said IGF-II promoter by PCR to produce a PCR product, and
ligating said PCR product with a vector.

7. A method for making a fish IGF-II promoter plasmid construct comprising the step of:
obtaining the IGF-II promoter fragment according to claim 2,
amplifying said IGF-II promoter fragment by PCR to produce a PCR product, and
ligating said PCR product with a vector.

8. A plasmid construct comprising:
the fish IGF-II promoter according to claim 1; and
a vector.

9. A plasmid construct comprising:
the recombinant fish IGF-II promoter according to claim 2; and
a vector.

10. An IGF-II promoter region comprising the DNA sequence of SEQ ID NO:13.

11. A method for determining the IGF-II promoter activity in a eukaryotic cell comprising:
ligating the IGF-II promoter according to claim 1 with a chloramphenicol acetyltransferase (CAT)-containing vector to form a plasmid construct;
transfecting said plasmid construct into said eukaryotic cell; and
measuring CAT activity.

12. A method for determining the IGF-II promoter fragment activity in a eukaryotic cell comprising:
ligating the IGF-II promoter fragment according to claim 2 with a chloramphenicol acetyltransferase (CAT) containing vector to form a plasmid construct; and
transfecting said plasmid construct into said eukaryotic cell; and
measuring CAT activity.

13. A method for expressing a coding sequence in a fish embryo comprising:
inserting the first IGF-II promoter region of claim 1 into a vector to form a plasmid construct having the coding sequence operatively linked to the first IGF-II promoter region, and intracytoplasmically injecting said plasmid construct to a fertilized fish egg, whereby said coding sequence is expressed.

14. A method for expressing a coding sequence in a fish embryo comprising:
inserting the recombinant IGF-II promoter of claim 2 into a vector to form a plasmid construct having the coding sequence operatively linked to the recombinant IGF-II promoter, and
intracytoplasmically injecting said plasmid construct to a fertilized fish egg, whereby said coding sequence is expressed.

15. A method for expressing a coding sequence in a fish embryo comprising:
inserting the IGF-II promoter region of claim 10 into a vector to form a plasmid construct having the coding sequence operatively linked to the IGF-II promoter region, and
intracytoplasmically injecting said plasmid construct to a fertilized fish egg, whereby said coding sequence is expressed.

16. The method for determining the IGF-II promoter activity in a eukaryotic cell according to claim 11, wherein said CAT containing vector is a pCAT-Basic vector.

17. The method for determining the IGF-II promoter activity in a eukaryotic cell according to claim 12, wherein said CAT containing vector is a pCAT-Basic vector.

18. The method for determining the IGF-II promoter activity in a eukaryotic cell according to claim 11, wherein said eukaryotic cell is a human lung large cell carcinoma cell.

19. The method for determining the IGF-II promoter activity in a eukaryotic cell according to claim 12, wherein said eukaryotic cell is a human lung large cell carcinoma cell.

\* \* \* \* \*

UNITED STATES PATENT AND TRADEMARK OFFICE
CERTIFICATE OF CORRECTION

PATENT NO. : 6,018,040
DATED : January 25, 2000
INVENTOR(S) : Jen-Leih WU; Jyh-Yih CHEN of Taiwan It is certified that error appears in the above-identified patent and that said Letters Patent is hereby corrected as shown below:

Page 1, column 1, line 1, in [54] title of the invention, amend "GROWTH FACTOR 11" to --- GROWTH FACTOR II ---.

Page 1, column 1, line 3, in [76] names of the inventor, amend the name of the first inventor "Jen-Lieh Wu" to --- Jen-Leih Wu ---.

Signed and Sealed this

Sixth Day of February, 2001

*Attest:*

Q. TODD DICKINSON

*Attesting Officer*  *Director of Patents and Trademarks*

SEQUENCE LISTING (1) GENERAL INFORMATION:

(iii) NUMBER OF SEQUENCES:33

(2) INFORMATION FOR SEQ ID NO:1:

(i) SEQUENCE CHARACTERISTICS:
      (A) LENGTH:450 bps
      (B) TYPE:nucleic acid
      (C) STRANDEDNESS:BOTH
      (D) TOPOLOGY:BOTH (ii) MOLECULE TYPE:cDNA to genomic RNA (iii) HYPOTHETICAL:No (xi) SEQUENCE DESCRIPTION: SEQ ID NO:1:

```
AGTGATTCCA CTGAATGTTA ATCTTAATTA CAGCAGGGCG GAGACATTGA CATTTTTCTT      60

GGAGTCGAAG GAATTACCCC TATTCTTGTT CAGTCTGCGT CCTGTGTGTA AACATTGTGA     120

TTGTAGGTTA CAGTGCGTAA ACGTGGAAAA TGCCCATGGA AGTGTTCCAT ATTTTGTGAC     180

TCTCACCCTC TTATTCTCCC TTCAAGCACT TTCATAAAAC GTCTCTGGGC CTTTTTTTTT     240

TCATGGGCGA AGAGGAGGAG CAAGGGGTGG GGTGGGTGTA AGGGGCGTGC TTTAGTATAT     300

AATACCTCTC CCTGAGAAGT TTTGCCTGTC GCCTAGTCTT TGGGACAGCT TCTCACTCAC     360

CATCTCTATA GTTTAACCAA CTGGGAAACT AACTCACCTG CAATCACACC AACCAAATAA     420

TTCCCAACAT TTTGACTACT GCCATCTGAC                                      450
```

(2) INFORMATION FOR SEQ ID NO:2:

(i) SEQUENCE CHARACTERISTICS:
      (A) LENGTH:50 bps
      (B) TYPE:nucleic acid
      (C) STRANDEDNESS:BOTH
      (D) TOPOLOGY:BOTH (ii) MOLECULE TYPE:cDNA to genomic RNA (iii) HYPOTHETICAL:No (xi) SEQUENCE DESCRIPTION:  SEQ ID NO:2:

AGTGATTCCA CTGAATGTTA ATCTTAATTA CAGCAGGGCG GAGACATTGA           50

(2) INFORMATION FOR SEQ ID NO:3:

(i) SEQUENCE CHARACTERISTICS:
            (A) LENGTH:50 bps
            (B) TYPE:nucleic acid
            (C) STRANDEDNESS:BOTH
            (D) TOPOLOGY:BOTH (ii) MOLECULE TYPE:cDNA to genomic RNA (iii) HYPOTHETICAL:No (xi) SEQUENCE DESCRIPTION:  SEQ ID NO:3:

CATTTTTCTT GGAGTCGAAG GAATTACCCC TATTCTTGTT CAGTCTGCGT           50

(2) INFORMATION FOR SEQ ID NO:4:

(i) SEQUENCE CHARACTERISTICS:
            (A) LENGTH:50 bps
            (B) TYPE:nucleic acid
            (C) STRANDEDNESS:BOTH
            (D) TOPOLOGY:BOTH (ii) MOLECULE TYPE:cDNA to genomic RNA (iii) HYPOTHETICAL:No (xi) SEQUENCE DESCRIPTION:  SEQ ID NO:4:

CCTGTGTGTA AACATTGTGA TTGTAGGTTA CAGTGCGTAA ACGTGGAAAA           50

(2) INFORMATION FOR SEQ ID NO:5:

(i) SEQUENCE CHARACTERISTICS:
            (A) LENGTH:50 bps
            (B) TYPE:nucleic acid
            (C) STRANDEDNESS:BOTH
            (D) TOPOLOGY:BOTH (ii) MOLECULE TYPE:cDNA to genomic RNA (iii) HYPOTHETICAL:No (xi) SEQUENCE DESCRIPTION:  SEQ ID NO:5:

TGCCCATGGA AGTGTTCCAT ATTTTGTGAC TCTCACCCTC TTATTCTCCC           50

(2) INFORMATION FOR SEQ ID NO:6:

(i) SEQUENCE CHARACTERISTICS:
            (A) LENGTH: 250 bps
            (B) TYPE:nucleic acid
            (C) STRANDEDNESS:BOTH
            (D) TOPOLOGY:BOTH (ii) MOLECULE TYPE:cDNA to genomic RNA (iii) HYPOTHETICAL:No (xi) SEQUENCE DESCRIPTION:  SEQ ID NO:6:

TTCAAGCACT TCATAAAAC GTCTCTGGGC CTTTTTTTTT TCATGGGCGA AGAGGAGGAG    60

CAAGGGGTGG GGTGGGTGTA AGGGGCGTGC TTTAGTATAT AATACCTCTC CCTGAGAAGT  120

TTTGCCTGTC GCCTAGTCTT TGGGACAGCT TCTCACTCAC CATCTCTATA GTTTAACCAA  180

```
CTGGGAAACT AACTCACCTG CAATCACACC AACCAAATAA TTCCCAACAT TTTGACTACT     240

GCCATCTGAC                                                           250

(2) INFORMATION FOR SEQ ID NO:7:

(i) SEQUENCE CHARACTERISTICS:
        (A) LENGTH: 21 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:7:

GGAAGCTTAG TGATTCCACT G                                               21

(2) INFORMATION FOR SEQ ID NO:8:

(i) SEQUENCE CHARACTERISTICS:
        (A) LENGTH: 24 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:8:

GGAAGCTTCA TTTTTCTTGG AGTC                                            24

(2) INFORMATION FOR SEQ ID NO:9:

(i) SEQUENCE CHARACTERISTICS:
        (A) LENGTH: 28 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:9:

CGCTGCAGCC TGTGTGTAAA CATTGTGA                                        28

(2) INFORMATION FOR SEQ ID NO:10:

(i) SEQUENCE CHARACTERISTICS:
        (A) LENGTH: 25 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:10:

GGAAGCTTTG CCCATGGAAG TGTTC                                           25

(2) INFORMATION FOR SEQ ID NO:11:

(i) SEQUENCE CHARACTERISTICS:
        (A) LENGTH: 28 bps
        (B) TYPE:nucleic acid
        (C) STRANDEDNESS:single stranded
```

(D) TOPOLOGY:linear (ii) MOLECULE TYPE:synthetic oligonucleotide (iii) HYPOTHETICAL:No (xi) SEQUENCE DESCRIPTION: SEQ ID NO:11:

CGCTGCAGTT CAAGCACTTT CATAAAAC                                28

(2) INFORMATION FOR SEQ ID NO:12:

(i) SEQUENCE CHARACTERISTICS:
        (A) LENGTH: 31 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:12:

GCGTCGACGT CAGATGGCAG TAGTCAAAAT G                             31

(2) INFORMATION FOR SEQ ID NO:13:

(i) SEQUENCE CHARACTERISTICS:
        (A) LENGTH:1001 bps
        (B) TYPE:nucleic acid
        (C) STRANDEDNESS:BOTH
        (D) TOPOLOGY:BOTH (ii) MOLECULE TYPE:CDNA to genomic RNA (iii) HYPOTHETICAL:No (xi) SEQUENCE DESCRIPTION: SEQ ID NO:13:

TGGTAAGCTT GCGACCGCCC TAGGACTAGT CTCGAGGCTA GCCCATGGGG CGCCGGGCCC    60
GGATCTGTGT TTGGTATATT TGATTTAAAC AGGGCTACAC AGATCCTGCC TACAGACAGA   120
GGAGGAGAAT GATTGGTGAC ATTGCCTTCA GATACAGATA GTGAGATGGG CCTTTTCCTA   180
AATACTGCGC ACACAACCAT AAGAAATAGA CATAAAAGTG AAATGTAATA ATTGTGTGCA   240
TATGTTTGTC CTCAGTGGGC AGTCGATCCC CAGACTGGAA TACACAGAGG AGGAGATCGG   300
CACATGGTAA GGGGCTCTTT CACGTTACTT TCCAATATTG ATAATATATG ACATGAAAAG   360
TTAAGTCTGA AGTAGCAGTG AGAATAAAAT CATAATTTAC AATGAACACA AAATGTTTTT   420
ATCTATTAAA ATACGTTTCA TTGTTATTTT GTTTTACTGT GAACACATTG TGCTCAACCC   480
AGCAACCAAT GAGTCATTTG CATATGAATG GTCTTTTATG GATGCTTTGG TAAATTTAAC   540
TTCAGATGGA GGGTGTCACT AGAATAAACT CGAGGTGACA GCTCGAGCTT GTCTGAATGA   600
AAACATATC CATAGCCTGA GAACAAAGTG TTGTTTGCAA TTCAATAGAT GTTTATCATT   660
TTACTTGAAC AGTTTAGGAC AAAAAAAAG GACACTAATG AATGAATTTA GTCACCAGAC   720
CAAGTAGAAA AATTATAGCA AAGTGCTTTT TCATAAGATT TATACGATAC AAGAAAAACA   780
CAGCATAATA AATAGTTAAA CATTGCAGGA TAAATCCAAT TTAAACACTG TTAATTAGGA   840
GGCGCATAAC ACTAACCATA ACTCTAAAAC TACACTGCAA TTTTACTTAT TTCCAAAGTT   900
TTTCCAAGAT TTTGATTTTA ATAAATGAAA CCTCAATTTT TATGTAATTA AATACTGATT   960
TAGGCGAGAA GTATATTCAA CCCTGAGGGA CTTGTACACC A                     1001

(2) INFORMATION FOR SEQ ID NO:14:

(i) SEQUENCE CHARACTERISTICS:

(A) LENGTH: 29 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:14:

CGGAATTCAT GGAAACCCAG CAAAGATAC                                29

(2) INFORMATION FOR SEQ ID NO:15:

(i) SEQUENCE CHARACTERISTICS:
        (A) LENGTH: 31 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:15:

CGGAATTCTC ATTTTGTGAC TGACAAAGTT G                             31

(2) INFORMATION FOR SEQ ID NO:16:

(i) SEQUENCE CHARACTERISTICS:
        (A) LENGTH: 30 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:16:

CGAAGCTTAG ATCMAAATTC RAKCCYATTC                               30

(2) INFORMATION FOR SEQ ID NO:17:

(i) SEQUENCE CHARACTERISTICS:
        (A) LENGTH: 31 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:17:

GTCTCGAGTT GTTTTTACAG TGAACCATTC C                             31

(2) INFORMATION FOR SEQ ID NO:18:

(i) SEQUENCE CHARACTERISTICS:
        (A) LENGTH: 34 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:18:

CGGGATCCGA AATAAAAGCC TCGCTCTCCA CAGA                          34

(2) INFORMATION FOR SEQ ID NO:19:

(i) SEQUENCE CHARACTERISTICS:
        (A) LENGTH: 36 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:19:

CGGGATCCAA TAAACCCAAC AGGCTATGGC CCCAGT                         36

(2) INFORMATION FOR SEQ ID NO:20:

(i) SEQUENCE CHARACTERISTICS:
        (A) LENGTH: 29 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:20:

CGGAATTCGG CCCTGAGACC CTGTGCGGG                            29

(2) INFORMATION FOR SEQ ID NO:21:

(i) SEQUENCE CHARACTERISTICS:
        (A) LENGTH: 29 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:21:

CGGAATTCAG AAATCTTGGG AGTCTTGAC                            29

(2) INFORMATION FOR SEQ ID NO:22:

(i) SEQUENCE CHARACTERISTICS:
        (A) LENGTH: 28 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:22:

CGCTCGAGCG CCCCTGTTGC CGTCGGAG                             28

(2) INFORMATION FOR SEQ ID NO:23:

(i) SEQUENCE CHARACTERISTICS:
        (A) LENGTH: 21 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:23:

GGTTGGCCTA CTGAAATAAA A                                          21

(2) INFORMATION FOR SEQ ID NO:24:

(i) SEQUENCE CHARACTERISTICS:
            (A) LENGTH: 26 bps
            (B) TYPE:nucleic acid
            (C) STRANDEDNESS:single stranded
            (D) TOPOLOGY:linear (ii) MOLECULE TYPE:synthetic oligonucleotide (iii) HYPOTHETICAL:No (xi) SEQUENCE DESCRIPTION: SEQ ID NO:24:

GGAAGCTTAT TTTTACATTT TCACTC                                     26

(2) INFORMATION FOR SEQ ID NO:25:

(i) SEQUENCE CHARACTERISTICS:
            (A) LENGTH: 26 bps
            (B) TYPE:nucleic acid
            (C) STRANDEDNESS:single stranded
            (D) TOPOLOGY:linear (ii) MOLECULE TYPE:synthetic oligonucleotide (iii) HYPOTHETICAL:No (xi) SEQUENCE DESCRIPTION: SEQ ID NO:25:

CGAAGCTTCG GTGCCAAATT ACGCAG                                     26

(2) INFORMATION FOR SEQ ID NO:26:

(i) SEQUENCE CHARACTERISTICS:
            (A) LENGTH: 26 bps
            (B) TYPE:nucleic acid
            (C) STRANDEDNESS:single stranded
            (D) TOPOLOGY:linear (ii) MOLECULE TYPE:synthetic oligonucleotide (iii) HYPOTHETICAL:No (xi) SEQUENCE DESCRIPTION: SEQ ID NO:26:

CGCTGCAGGA CATTTTCAAC AGGAAA                                     26

(2) INFORMATION FOR SEQ ID NO:27:

(i) SEQUENCE CHARACTERISTICS:
            (A) LENGTH: 30 bps
            (B) TYPE:nucleic acid
            (C) STRANDEDNESS:single stranded
            (D) TOPOLOGY:linear (ii) MOLECULE TYPE:synthetic oligonucleotide (iii) HYPOTHETICAL:No (xi) SEQUENCE DESCRIPTION: SEQ ID NO:27:

CGAAGCTTGC TGGTGGTGGT GGTGGGGCTG                                 30

(2) INFORMATION FOR SEQ ID NO:28:

(i) SEQUENCE CHARACTERISTICS:
            (A) LENGTH: 26 bps
            (B) TYPE:nucleic acid

```
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:28:

CGCTGCAGGA CTTTGTTCCA TTGCGC                                          26

(2) INFORMATION FOR SEQ ID NO:29:

(i) SEQUENCE CHARACTERISTICS:
        (A) LENGTH: 25 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:29:

GCCTGCAGTT CCAACAAGAC AAAGC                                           25

(2) INFORMATION FOR SEQ ID NO:30:

(i) SEQUENCE CHARACTERISTICS:
        (A) LENGTH: 23 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:30:

GGAAGCTTCA TGCCTGCATC TAC                                             23

(2) INFORMATION FOR SEQ ID NO:31:

(i) SEQUENCE CHARACTERISTICS:
        (A) LENGTH: 22 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:31:

GGAAGCTTCT GCATCAACCC CG                                              22

(2) INFORMATION FOR SEQ ID NO:32:

(i) SEQUENCE CHARACTERISTICS:
        (A) LENGTH: 27 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION:  SEQ ID NO:32:

TTCACCGGGG TGGTGCCCAT CCTGGTC                                         27
```

(2) INFORMATION FOR SEQ ID NO:33:

(i) SEQUENCE CHARACTERISTICS:
        (A) LENGTH: 30 bps
        (B) TYPE:nucleic acid
        (C) STRANDEDNESS:single stranded
        (D) TOPOLOGY:linear (ii) MOLECULE TYPE:synthetic oligonucleotide (iii) HYPOTHETICAL:No (xi) SEQUENCE DESCRIPTION: SEQ ID NO:33:

TGAAGAAGAT GGTGCGCTCC TGGACGTAGC       30